US008968335B2

(12) United States Patent  
Robinson et al.

(10) Patent No.: US 8,968,335 B2  
(45) Date of Patent: Mar. 3, 2015

(54) HAND OPERATED DEVICE FOR CONTROLLED DEPLOYMENT OF A TISSUE ANCHOR AND METHOD OF USING THE SAME

(75) Inventors: Jason H. Robinson, Windham, NH (US); Steven Cahalane, Pelham, NH (US); Megan E. Holmes, Nashua, NH (US); Christopher C. Lee, Tewksbury, MA (US); Michael W. Sutherland, Lowell, MA (US); Aaron M. Call, Mesa, AZ (US); James M. Sellers, Eliot, ME (US); Michael R. Cole, Stratham, NH (US); Gregory J. Kenny, Wakefield, MA (US); Mathew S. Cardinali, Berwick, ME (US)

(73) Assignee: Mitralign, Inc., Tewksbury, MA (US)

( * ) Notice: Subject to any disclaimer, the term of this patent is extended or adjusted under 35 U.S.C. 154(b) by 489 days.

(21) Appl. No.: 13/282,139

(22) Filed: Oct. 26, 2011

(65) Prior Publication Data

US 2012/0109155 A1     May 3, 2012

Related U.S. Application Data

(60) Provisional application No. 61/407,341, filed on Oct. 27, 2010.

(51) Int. Cl.  
*A61B 17/10* (2006.01)  
*A61B 17/04* (2006.01)  
(Continued)

(52) U.S. Cl.  
CPC ......... *A61B 17/0401* (2013.01); *A61B 17/0487* (2013.01); *A61B 17/2833* (2013.01); *A61B 18/1492* (2013.01); *A61B 2017/00243* (2013.01); *A61B 2017/003* (2013.01); *A61B 2017/0046* (2013.01); *A61B 2017/0409* (2013.01); *A61B 2017/0417* (2013.01); *A61B 2017/0419* (2013.01); *A61B 2017/0458* (2013.01); *A61B 2017/0464* (2013.01); *A61B 2017/048* (2013.01); *A61B 2017/0496* (2013.01); *A61B 2017/22038* (2013.01); *A61B 2017/22074* (2013.01); *A61B 2017/3447* (2013.01);  
(Continued)

(58) Field of Classification Search  
USPC .................................. 606/139, 144, 146, 148  
See application file for complete search history.

(56) References Cited

U.S. PATENT DOCUMENTS 5,693,059 A * 12/1997 Yoon ............................. 606/139  
7,713,278 B2 * 5/2010 Hess et al. .................... 606/153  
(Continued)

FOREIGN PATENT DOCUMENTS

WO     WO2004/098701     11/2004

*Primary Examiner* — Elizabeth Houston  
*Assistant Examiner* — Robert Lynch  
(74) *Attorney, Agent, or Firm* — Leason Ellis LLP

(57) ABSTRACT

A tissue anchoring system includes a tissue anchor member that is suitable for anchoring against tissue. The system also includes a tensioning member operatively connected to the anchor member such that the anchor member can slide relative to the tensioning member, the tensioning member capable of being pulled to cause the anchor member to move relative to the tensioning member into a position seated against the tissue. A hand operated deployment catheter is operable to extend and deploy the anchor member therefrom. The deployment catheter includes a rotatable member about which the tensioning member is routed and a clutch assembly for limiting tension within the tensioning member to prevent the deployed anchor from being pulled through the tissue.

20 Claims, 26 Drawing Sheets

(51) Int. Cl.
  *A61B 17/28* (2006.01)
  *A61B 18/14* (2006.01)
  *A61B 17/00* (2006.01)
  *A61B 17/22* (2006.01)
  *A61B 17/34* (2006.01)
  *A61B 18/00* (2006.01)
  *A61B 19/00* (2006.01)
  *A61M 25/04* (2006.01)

(52) U.S. Cl.
  CPC ......... *A61B 2018/00357* (2013.01); *A61B 2018/00601* (2013.01); *A61B 2018/144* (2013.01); *A61B 2019/5466* (2013.01); *A61M 25/04* (2013.01)

USPC .................................. 606/139; 606/146

(56) References Cited

U.S. PATENT DOCUMENTS

| | | | | |
|---|---|---|---|---|
| 7,824,443 | B2* | 11/2010 | Salahieh et al. | 623/2.11 |
| 2008/0228165 | A1 | 9/2008 | Spence et al. | |
| 2008/0228267 | A1* | 9/2008 | Spence et al. | 623/2.36 |
| 2009/0163934 | A1 | 6/2009 | Raschdorf et al. | |
| 2009/0240206 | A1* | 9/2009 | Lunn et al. | 604/175 |
| 2010/0016655 | A1 | 1/2010 | Annest et al. | |

* cited by examiner

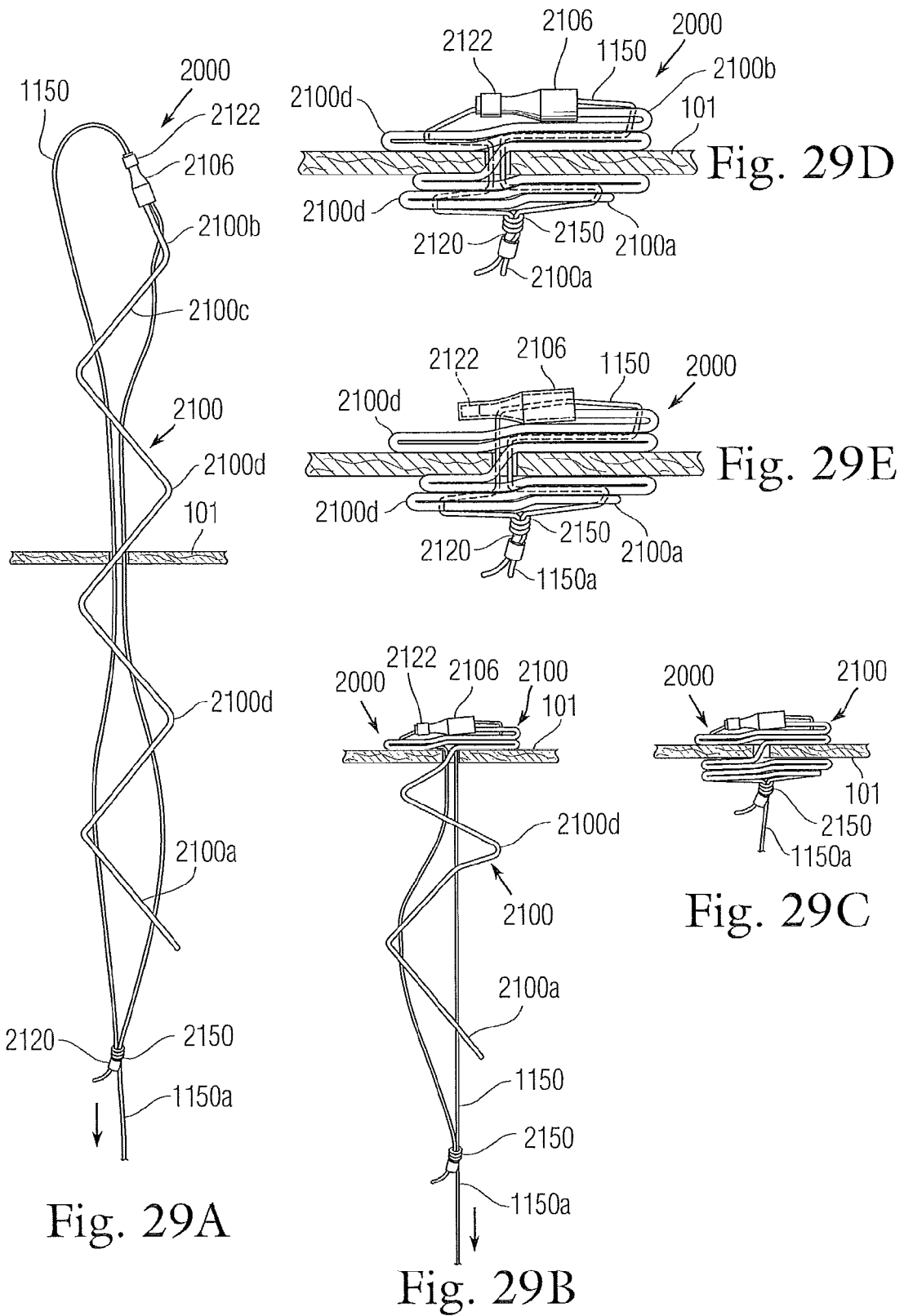

HAND OPERATED DEVICE FOR CONTROLLED DEPLOYMENT OF A TISSUE ANCHOR AND METHOD OF USING THE SAME

CROSS REFERENCE TO RELATED APPLICATION

The present application claims priority to and the benefit of U.S. Patent Application No. 61/407,341, filed Oct. 27, 2010, which is hereby incorporated by reference in its entirety.

TECHNICAL FIELD

The present invention relates to tissue fastening, and in particular, to a tissue fastening performed in a minimally invasive and percutaneous manner using an hand operated instrument.

BACKGROUND

Referring initially to FIGS. 1-4 solely for purposes of understanding the anatomy of a heart 10, and specifically the left side of the heart 10, the left atrium (LA) 12 and left ventricle (LV) 14 are shown. An aorta 16 receives oxygenated blood from left ventricle 14 through an aortic valve 18, which serves to prevent regurgitation of blood back into left ventricle 14. A mitral valve 20 is positioned between left atrium 12 and left ventricle 14, and allows one-way flow of the oxygenated blood from the left atrium 12 to the left ventricle 14.

Mitral valve 20, which will be described below in more detail, includes an anterior leaflet 22 and a posterior leaflet 24 that are coupled to cordae tendonae 26, 28 (FIG. 4). Cordea tendonae 26, 28 serve as "tension members" that prevent the leaflets 22, 24 of mitral valve 20 from moving past their closing point and prolapsing back into the left atrium 12. When left ventricle 14 contracts during systole, cordae tendonae 26, 28 limit the upward motion (toward the left atrium) of the anterior and posterior leaflets 22, 24 past the point at which the anterior and posterior leaflets 22, 24 meet and seal to prevent backflow from the left ventricle 14 to the left atrium 12 ("mitral regurgitation" or "mitral insufficiency"). Cordae tendonae 26, 28 arise from a columnae carnae or, more specifically, a musculi papillares (papillary muscles) of the columnae carnae. In various figures herein, some anatomical features have been deleted solely for clarity.

Anterior leaflet 22 and posterior leaflet 24 of the mitral valve 20 are generally thin, flexible membranes. When mitral valve 20 is closed, anterior leaflet 22 and posterior leaflet 24 are generally aligned and contact one another along a "line of coaptation" several millimeters back from their free edges, to create a seal that prevents mitral regurgitation. Alternatively, when mitral valve 20 is opened, blood flows downwardly through an opening created between anterior leaflet 22 and posterior leaflet 24 into left ventricle 14.

Many problems relating to the mitral valve may occur and may cause many types of ailments. Such problems include, but are not limited to, mitral regurgitation. Mitral regurgitation, or leakage, is the backflow of blood from left ventricle 14 into the left atrium 12 due to an imperfect closure of mitral valve 20. That is, leakage often occurs when the anterior and posterior leaflets 22, 24 do not seal against each other, resulting in a gap between anterior leaflet 22 and posterior leaflet 24 when the leaflets are supposed to be fully coapted during systole.

In general, a relatively significant systolic gap may exist between anterior leaflet 22 and posterior leaflet 24 for a variety of different reasons. For example, a gap may exist due to congenital malformations, because of ischemic disease, or because the heart 10 has been damaged by a previous heart attack. Such a gap may also be created when congestive heart failure, e.g., cardiomyopathy, or some other type of distress which causes a heart 10 to be enlarged. Enlargement of the heart 10 can result in dilation (stretching) of the mitral annulus. This enlargement is usually limited to the posterior valve annulus and is associated with the posterior leaflet 24, because the anterior annulus is a relatively rigid fibrous structure. When the posterior annulus enlarges, it causes the posterior leaflet 24 to move away from the anterior leaflet 22, causing a gap during systole because the two leaflets no longer form proper coaptation. This results in leakage of blood through the valve 20, or regurgitation.

Blood leakage through mitral valve 20 generally causes a heart 10 to operate less efficiently, as the heart 10 pumps blood both out to the body via the aorta 16, and also back (in the form of mitral regurgitation) into the left atrium 12. Leakage through mitral valve 20, or general mitral insufficiency, is thus often considered to be a precursor to congestive heart failure (CHF) or a cause of progressive worsening of heart failure. There are generally different levels of symptoms associated with heart failure. These levels are classified by the New York Heart Association (NYHA) functional classification system. The levels range from a Class 1 level which is associated with an asymptomatic patient who has substantially no physical limitations to a Class 4 level which is associated with a patient who is unable to carry out any physical activity without discomfort and has symptoms of cardiac insufficiency even at rest. In general, correcting or reducing the degree of mitral valve leakage may be successful in allowing the NYHA classification grade of a patient to be reduced. For instance, a patient with a Class 4 classification may have his classification reduced to Class 3 or Class 2 and, hence, be relatively comfortable at rest or even during mild physical exertion. By eliminating the flow of blood backwards into the left atrium 12, therapies that reduce mitral insufficiency reduce the workload of the heart 10 and may prevent or slow the degradation of heart function and congestive heart failure symptoms that is common when a significant degree of mitral insufficiency remains uncorrected.

Treatments used to correct for mitral valve leakage or, more generally, CHF, are typically highly invasive, open-heart surgical procedures. In extreme cases, this may include implantation of a ventricular assist device such as an artificial heart in a patient with a failing heart. The implantation of a ventricular assist device is often expensive, and a patient with a ventricular assist device must be placed on extended anti-coagulant therapy. Anti-coagulant therapy reduces the risk of blood clot formation for example, within the ventricular assist device. Reducing the risks of blood clots associated with the ventricular assist device is desirable, but anti-coagulant therapies may increase the risk of uncontrollable bleeding in a patient, e.g., as a result of a fall.

Rather than implanting a ventricular assist device, bi-ventricular pacing devices similar to pacemakers may be implanted in some cases, e.g., cases in which a heart beats inefficiently in a particular asynchronous manner. While the implantation of a bi-ventricular pacing device may be effective, not all heart patients are suitable for receiving a bi-ventricular pacing device. Further, the implantation of a bi-ventricular pacing device is expensive, and is generally not effective in significantly reducing or eliminating the degree of mitral regurgitation.

Open-heart surgical procedures that are intended to correct for mitral valve leakage, specifically, can involve the implantation of a replacement valve. Valves from animals, e.g., pigs, may be used to replace a mitral valve 20 in a human. While a pig valve may relatively successfully replace a mitral valve, such replacement valves generally wear out, thereby requiring additional open surgery at a later date. Mechanical valves, which are less likely to wear out, may also be used to replace a leaking mitral valve. However, when a mechanical valve is implanted, there is an increased risk of thromboembolism, and a patient is generally required to undergo extended anti-coagulant therapies.

A less invasive surgical procedure involves heart bypass surgery associated with a port access procedure. For a port access procedure, the heart may be accessed by cutting between ribs or sometimes removing parts of one or more ribs, as opposed to dividing the sternum to open the entire chest of a patient.

One open-heart surgical procedure that is particularly successful in correcting for mitral valve leakage and, in addition, mitral regurgitation, is an annuloplasty procedure. During an annuloplasty procedure, a medical device such as an annuloplasty ring may be implanted surgically on the left atrial side of mitral annulus (i.e., generally the attachment location of the base of the mitral valve to the heart). The device reduces a dilated mitral valve annulus to a relatively normal size and, specifically, moves the posterior leaflet closer to the anterior leaflet to aid anterior-posterior leaflet coaptation and thus improve the quality of mitral valve closure during systole. Annuloplasty rings are often shaped substantially like the letter "D" to correspond to the natural shape of the mitral annulus as viewed from above. Typically, the rings are formed from a rod or tube of biocompatible material, e.g., plastic, that has a DACRON mesh covering.

In order for an annuloplasty ring to be implanted, a surgeon surgically attaches the annuloplasty ring to the mitral valve on the atrial side of the mitral valve. Conventional methods for installing a ring require open-heart surgery which involves opening a patient's sternum and placing the patient on a heart bypass machine. The annuloplasty ring is sewn on a top portion of the mitral valve. In sewing the annuloplasty ring onto the mitral valve, a surgeon generally sews the straight side of the "D" to the fibrous tissue located at the junction between the posterior wall of the aorta and the base of the anterior mitral valve leaflet. As the curved part of the ring is sewn to the posterior aspect of the annulus, the surgeon alternately acquires a relatively larger amount of tissue from the mitral annulus, e.g., a one-eighth inch bite of tissue, using a needle and thread, compared to a relatively smaller bite taken of the fabric covering of the annuloplasty ring. Once the thread has loosely coupled the annuloplasty ring to the mitral valve annulus tissue, the annuloplasty ring is slid into contact with the mitral annulus. The tissue of the posterior mitral annulus that was previously stretched out, e.g., due to an enlarged heart, is effectively reduced in circumference and pulled forwards towards the anterior mitral leaflet by the tension applied by annuloplasty ring with the suture or thread. As a result, a gap between anterior leaflet 22 and posterior leaflet 24 during ventricular contraction or systole may be reduced and even substantially closed off in many cases thereby significantly reducing or even eliminating mitral insufficiency. After the mitral valve 20 is shaped by the ring, the anterior and posterior leaflets 22, 24 will reform typically by pulling the posterior leaflet 24 forward to properly meet the anterior leaflet 22 and create a new contact line that will enable mitral valve 20 to appear and to function properly.

Although a patient that receives an annuloplasty ring may be subjected to anti-coagulant therapies, the therapies are not extensive, as a patient is only subjected to the therapies for a matter of weeks, e.g., until tissue grows over the annuloplasty ring.

Another type of procedure that is generally effective in reducing mitral valve leakage associated with prolapse of the valve leaflets involves placing a single edge-to-edge suture in the mitral valve 20 that apposes the mid-portions of anterior and posterior leaflets 22, 24. For example, in an Alfieri stitch or a bow-tie repair procedure, an edge-to-edge stitch is made at approximately the center of the gap between an anterior leaflet 22 and a posterior leaflet 24 of a mitral valve 20. Once the stitch is in place between the anterior and posterior leaflets 22, 24, it is pulled in to form a suture which holds anterior leaflet 22 against posterior leaflet 24.

Another surgical procedure that reduces mitral valve leakage involves placing sutures along a mitral valve annulus around the posterior leaflet 24. These sutures may be formed as a double track, e.g., in two "rows" from a single strand of suture material. The sutures are tied off at approximately a central point (P2) of posterior leaflet 24. Pledgets are often positioned under selected sutures to prevent the sutures from tearing through annulus 40. When the sutures are tightened and tied off, the circumference of the annulus 40 may effectively be reduced to a desired size such that the size of a systolic gap between posterior leaflet 24 and an anterior leaflet 22 may be reduced.

While invasive surgical procedures have proven to be effective in the treatment of mitral valve leakage, invasive surgical procedures often have significant drawbacks. Any time a patient undergoes open-heart surgery, there is a risk of infection. Opening the sternum and using a cardiopulmonary bypass machine has also been shown to result in a significant incidence of both short and long term neurological deficits. Further, given the complexity of open-heart surgery, and the significant associated recovery time, people that are not greatly inconvenienced by CHF symptoms, e.g., people at a Class 1 classification, may choose not to have corrective surgery. In addition, people that need open heart surgery the most, e.g., people at a Class 4 classification, may either be too frail or too weak to undergo the surgery. Hence, many people that may benefit from a surgically repaired mitral valve may not undergo surgery.

In another method, a cinching device is placed within the coronary sinus (CS) using a catheter system, with distal, mid, and proximal anchors within the lumen of the CS to allow plication of the annulus 40 via the CS. In practice, these anchors are cinched together and the distance between them is shortened by pulling a flexible tensile member such as a cable or suture with the intent being to shorten the valve annulus 40 and pull the posterior leaflet 24 closer to the anterior leaflet 22 in a manner similar to an annuloplasty procedure. Unfortunately, since the tissue that forms the CS is relatively delicate, the anchors are prone to tear the tissue during the cinching procedure. In addition, the effect on the mitral annulus may be reduced when the CS of a particular patient is not directly aligned with the mitral annulus. Other minimally invasive techniques have been proposed but have various drawbacks related to such factors as effectiveness and/or accuracy of catheter-based implementation.

SUMMARY

In one embodiment, a tissue anchoring system includes a tissue anchor member that is suitable for deployment and for anchoring against tissue. The system also includes a tensioning member operatively connected to the anchor member such that the anchor member can slide relative to the tensioning member, the tensioning member capable of being pulled to cause the anchor member to move and seat against the tissue. A hand operated deployment catheter is operable to extend and deploy the anchor member therefrom. The deployment catheter includes a rotatable member about which the tensioning member is routed and a clutch assembly for limiting tension within the tensioning member.

In another embodiment, a tissue anchoring system for deploying a tissue anchor includes an anchor member capable of being inserted through tissue and suitable for anchoring against at least one side of the tissue. The system also includes a tensioning member operatively connected to the anchor member such that the anchor member can slide relative to the tensioning member, the tensioning member capable of being pulled to cause the anchor member to move relative to the tensioning member. As described herein, any number of different types of tissue anchors can be used in accordance with the present invention.

The system further includes a deployment catheter operable to extend and deploy the anchor member therefrom. The deployment catheter includes a handle and a catheter body that is fixedly attached to the handle at one end. The anchor member and connected tensioning member are contained within a main lumen of the catheter body. The catheter includes a spool assembly including a spool about which the tensioning member is routed and a slip clutch assembly that is operatively coupled to the spool assembly. The slip clutch assembly is configured to limit tension within the tensioning member as the tensioning member is pulled and wound about the spool as the anchor member is being moved into position and more particularly, the slip clutch assembly is configured to prevent tissue pull through. In other words, the slip clutch assembly is configured to limit the force applied to an atrial anchor to prevent tissue pull through (e.g., prevent the anchor from being pulled through the tissue itself).

A deployable pusher assembly is provided for controllably deploying a portion of the anchor member. The pusher assembly includes a slideable pusher actuator that is coupled to and accessible along the handle and is moveable between a retracted position and an extended position in which the pusher assembly deploys at least a portion of the anchor member.

These and other aspects, features and advantages shall be apparent from the accompanying Drawings and description of certain embodiments of the invention.

BRIEF DESCRIPTION OF THE DRAWINGS

FIGS. 29A-29E are respective side views illustrating a sequence of steps used for securing a tissue anchor to a layer of tissue.

DETAILED DESCRIPTION OF CERTAIN EMBODIMENTS OF THE INVENTION

Reference will be made to the various figures in describing the methods, devices and systems in various forms useful to the purpose of plicating tissue, for example, and particularly useful for plicating annulus tissue associated with the mitral valve of a patient. It will be appreciated that although specific details of the methods, devices and systems will be given herein, many different changes, substitutions and additions may be made to such details by those of ordinary skill while still falling within the inventive aspects more generally set forth herein and understood by those of ordinary skill upon review of the present disclosure in its entirety. It should be noted that the terms "proximal" and "distal" are used, as conventional in the art, to denote spatial relationship relative to the person using the particular device or component. That is, "proximal" refers to a position closer to the user and "distal" refers to a position farther from the user.

Figure 1:
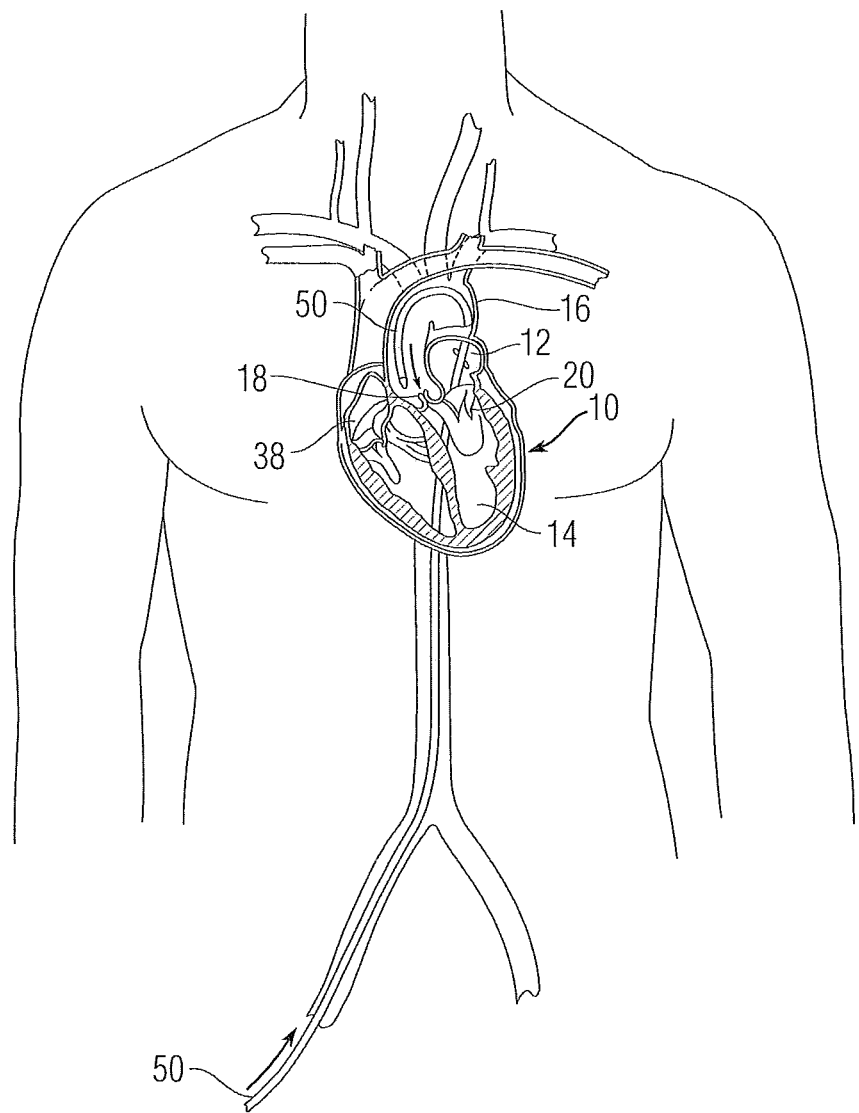
FIG. 1 is a schematic illustration of a patient with the anatomy of the heart in cross section and a guide catheter introduced through the vascular system into the aorta and heart of the patient.
Figure 2:
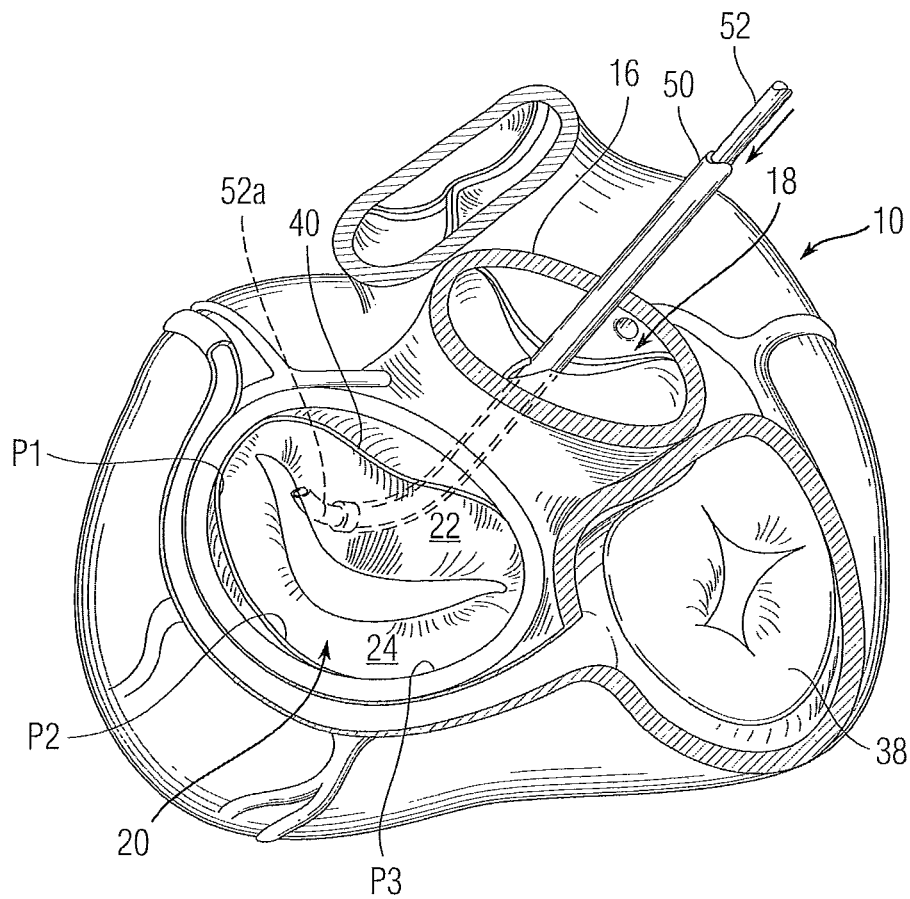
FIG. 2 is a cross sectional view of the heart from above showing the introduction of various catheters.
Figure 3:
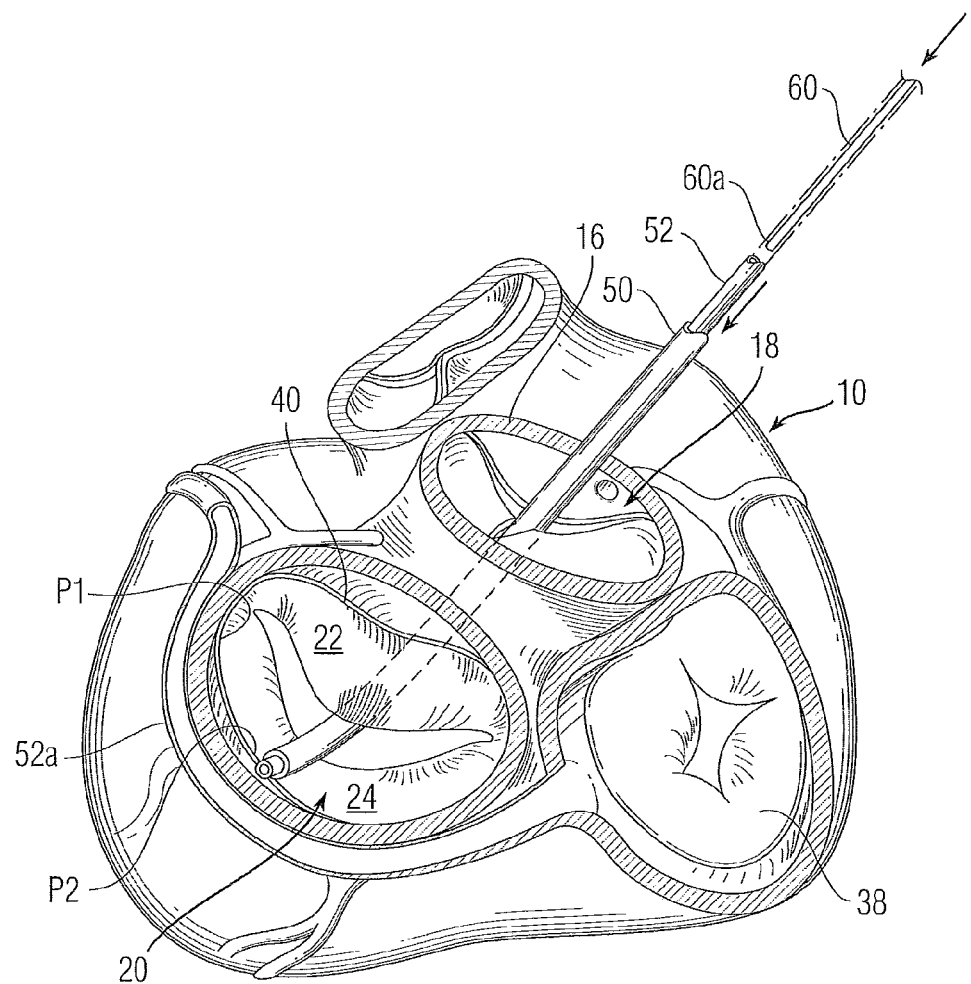
FIG. 3 is a cross sectional view of the heart similar to FIG. 2 and illustrating the further introduction of a guide wire.
Figure 4:
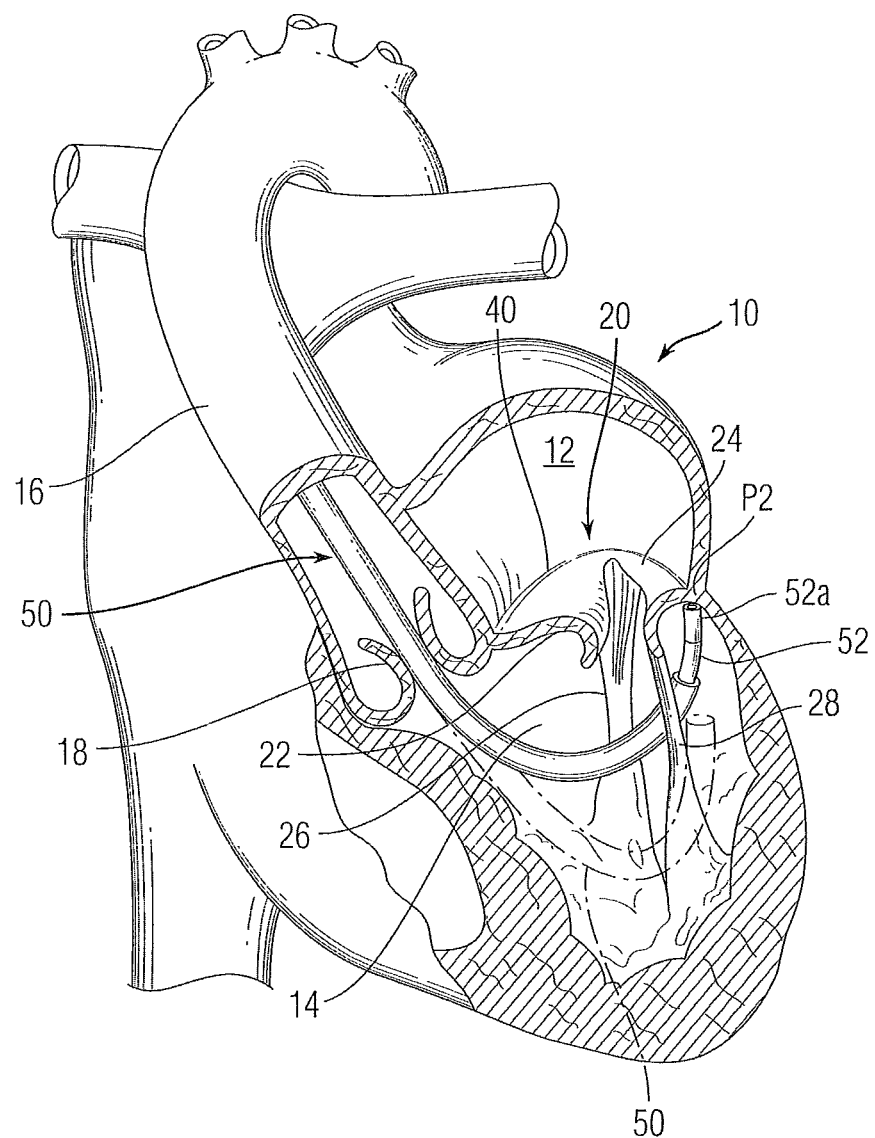
FIG. 4 is a partial longitudinal cross sectional view of the heart showing the positioning of the catheters in the left ventricle and coronary sinus.

It will be appreciated that the instruments and techniques described with reference to FIGS. 1-9 are merely exemplary in nature and as discussed herein, other techniques can be used for positioning and placing guide wires that are used in a subsequent procedure for delivering an anchor to the target tissue. Referring first to FIGS. 1-4, a guide catheter 50 is illustrated as being directed into the vascular system of a patient, such as through an artery in the groin region of the patient, as shown in FIG. 1. The guide catheter 50 may be a 12 mm catheter directed through the vascular system in any suitable manner. As shown, guide catheter 50 is directed into the aorta 16, through the aortic valve 18 and into the left ventricle 14 between the pair of cordae tendonae 26, 28 as best shown in FIG. 4. This guide catheter 50 is then used as a guide sheath or tube for guiding all of the subsequent catheter devices into the left ventricle 14 for use in a method of plicating the annulus 40 of the mitral valve 20. It will be appreciated that other methods of guidance may be used as alternatives or in a supplemental fashion to the various methods disclosed herein. After initial insertion of the guide catheter 50, a P2 catheter 52 is inserted to the guide catheter 50. As known in the art, "P2" refers to the central location of the base of the posterior leaflet 24 along the annulus 40. The P2 catheter 52 may have a deflectable tip to allow more accurate and easier manipulation and location of the catheter tip relative to the annulus 40. The catheter tip can include a radiopaque marker 52a visible under a fluoroscope. The distal tip 52a of the P2 catheter 52 is aligned at the annulus 40 as shown in FIG. 4 such that it is directed upward at the interior of the left atrium 12.

As an alternative to using a guide catheter 50 and P2 catheter S2, a single steerable guide sheath can be used and positioned at the desired location on the ventricular side of the mitral annulus for deployment of the guide wire.

Figure 5:
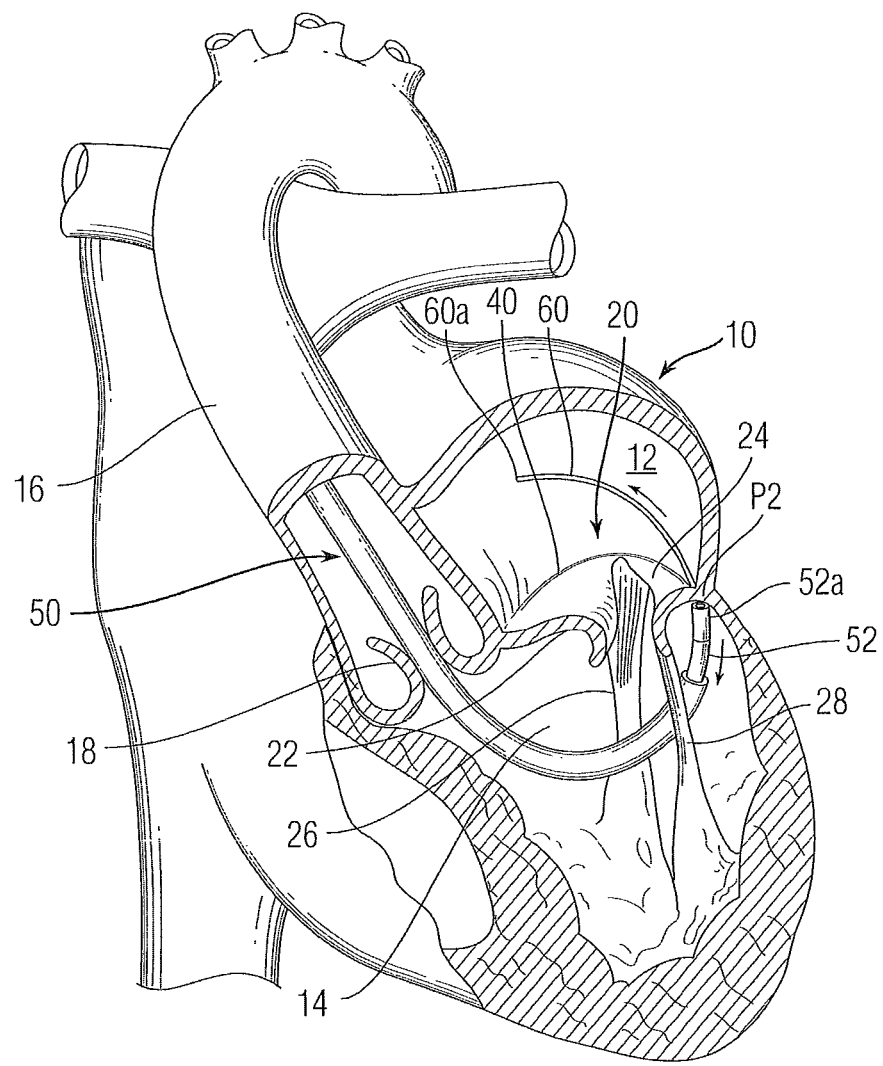
FIG. 5 is a cross sectional view of the heart similar to FIG. 4, but illustrating the further introduction of a guide wire through the mitral valve annulus.

Referring to FIG. 5, when accurate positioning of the P2 catheter 52 has been confirmed using a fluoroscope, for example, a first RF guide wire may be introduced through the P2 catheter. The P2 guide wire may have a radio frequency (RF) energy delivery tip 60a for assisting with penetration through mitral tissue generally at the annulus 40. For this purpose, a suitable RF energy device (not shown) may be coupled to guide wire 60, as well as the other RF guide wires disclosed hereinbelow. The distal portion of the P2 guide wire 60 then extends into the left atrium and curls back on itself to help prevent tissue damage within the left atrium 12 as shown best in FIG. 6.

The method then involves the further introduction of a P1 guide wire 62 through the use of a double lumen catheter 70 contained within a sheath 72. Double lumen catheter 70 and sheath 72 are introduced into the guide catheter 50 after withdrawal of the P2 catheter 52 therefrom. Alternatively, guide catheter 50 can be a steerable guide sheath and deployed in close proximity to the mitral annulus and sheath 72 can be omitted. Double lumen catheter 70 more specifically comprises a central or first catheter member 74 having a lumen 74a threaded over the P2 guide wire 60. In addition to this first or P2 catheter member 74, double lumen catheter 70 further comprises second catheter member 76 corresponding generally to the P1 location generally along the posterior mitral annulus 40. The second and third catheter member 76 also includes lumen 76a containing guide wire 62. It will be appreciated that other locations along the annulus 40 may be chosen in addition to or instead of those discussed illustratively herein.

Figure 7:
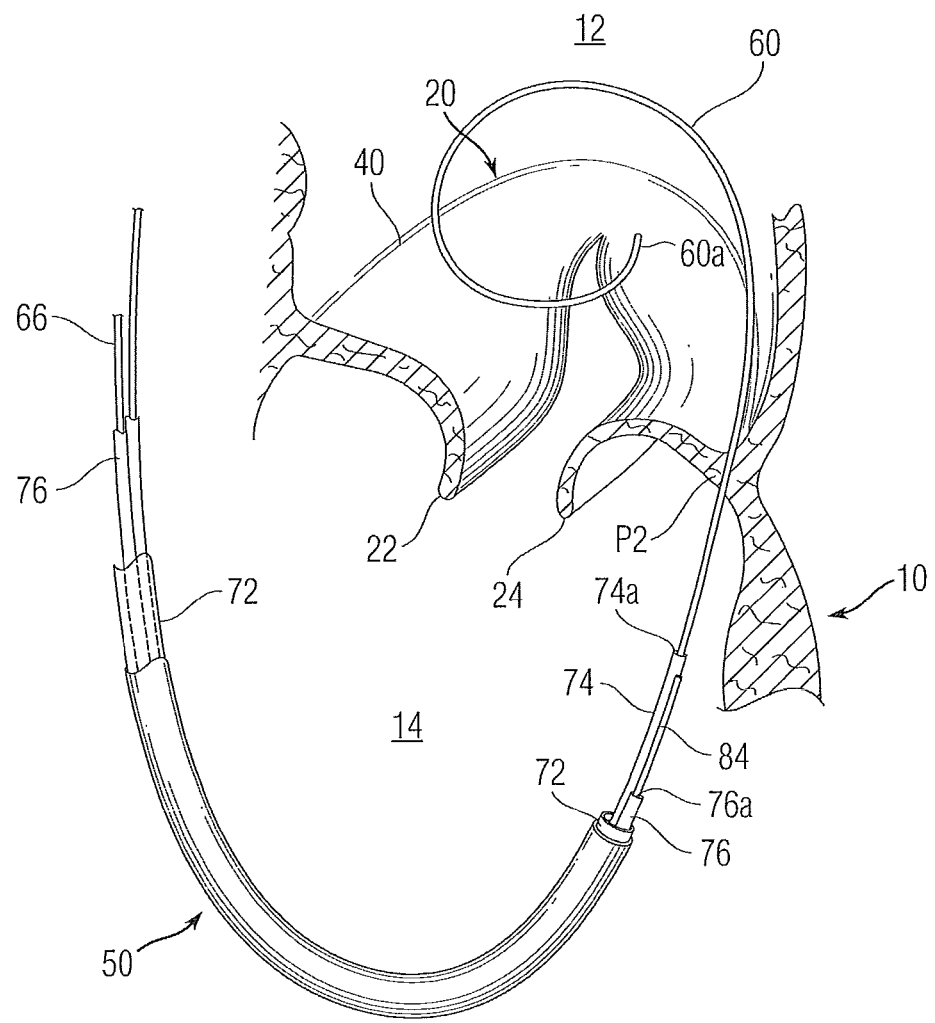
FIG. 7 is a cross sectional view of the mitral valve similar to FIG. 6 and showing the further introduction of the expandable triple lumen catheter.
Figure 8:
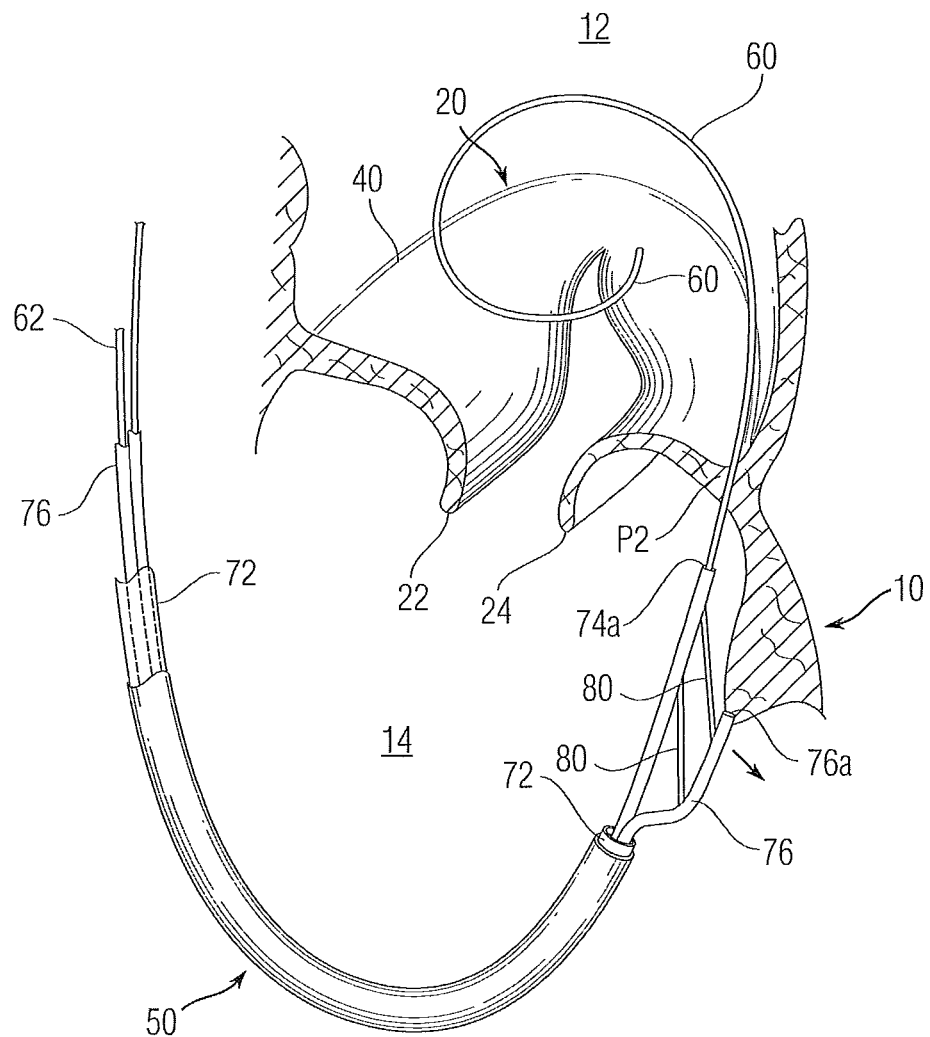
FIG. 8 is a cross sectional view of the heart similar to FIG. 7, but illustrating the initial expansion of the triple lumen catheter.
Figure 9:
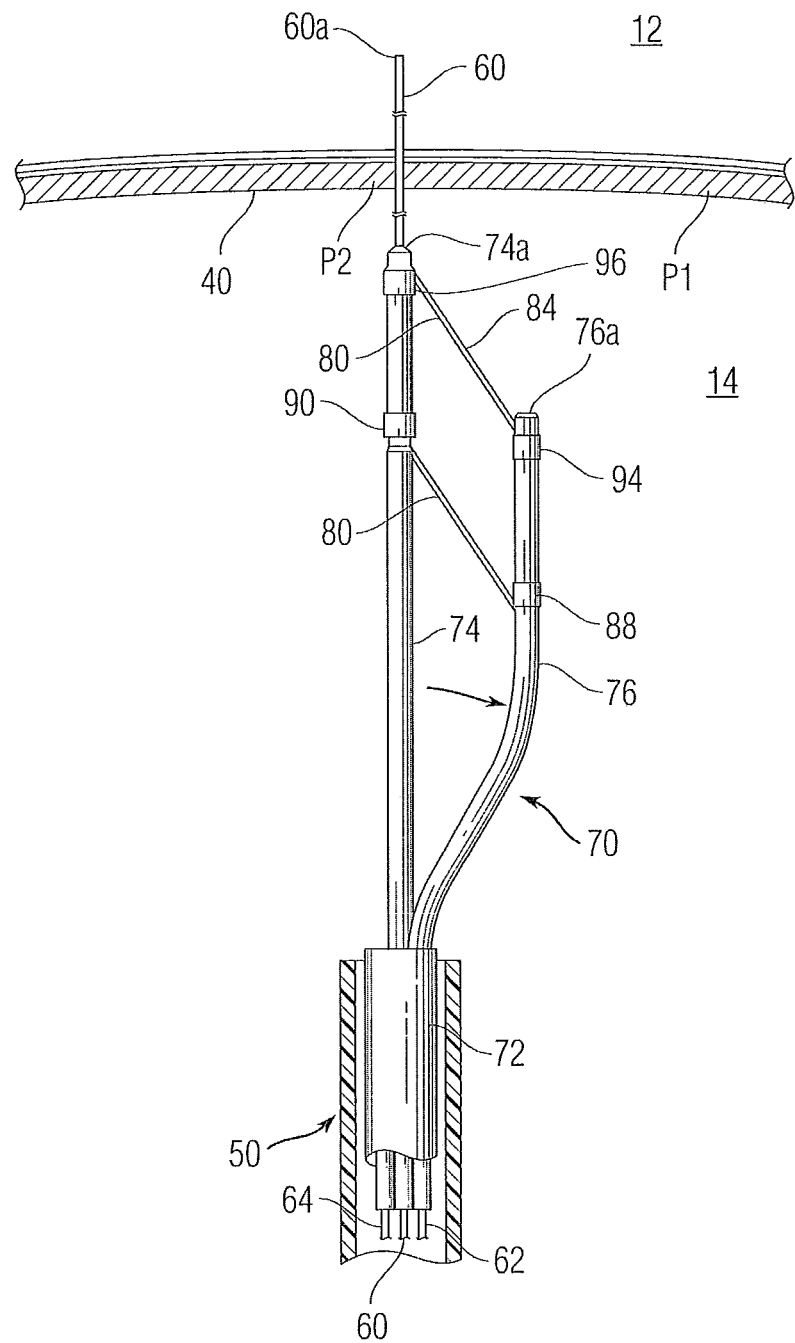
FIG. 9 is an elevational view of the expanding triple lumen catheter relative to the mitral valve annulus.

As further shown in FIG. 7, the combined double lumen catheter 70 and sheath 72 are pushed through the guide catheter 50 and an expandable distal portion comprised of catheter members 74, 76 is then extended from the sheath 72 in the left ventricle 14 of the patient. The initial positioning of the P2 guide wire 60 ensures that the middle or P2 catheter member 74 will be an accurate reference point at P2. When the sheath 72 reaches the distal location shown in FIGS. 7-9, the double lumen catheter 70 is pushed outward from the distal end of the sheath 72 and expansion takes place as shown in FIGS. 8 and 9. As best shown in FIG. 9, the outer catheter member 76 (that is, the P1 catheter member) automatically expand outward due to their coupling with the central or P2 catheter member 74 by way of connecting bars 80, 84. These connecting bars may, for example, be formed from thin metallic plate material such as superelastic material, stainless steel, other metals or combinations of materials. It has been found that a thin plate of Nitinol™ (nickel-titanium) stacked adjacent to a thin plate of stainless steel works well for each connecting bar 80, 84. The Nitinol exhibits spring characteristics effective for the expansion of the two outer catheter member 76 away from the inner or central catheter member 74, while the stainless steel plate of each connecting bar provides additional stiffness for support purposes.

Respective connectors 88, 90, 94, 96 couple each connecting bar 80, 84 to the respective catheter members 76, 74 as shown in FIG. 9 with a living hinge adjacent each connector 88, 90, 94, 96. This illustrative structure therefore essentially forms a four-bar type linkage structure being formed by catheter members 74, 76 and bars 80, 84. This expandable structure therefore causes the outer catheter member 76 to translate distally and also expand laterally outward to known positions dictated by the respective lengths of the bars 80, 84. In this example, the distal end of catheter 76 is ultimately positioned approximately at position P1 along the mitral annulus 40. It will be appreciated that these positions are representative and illustrative only and that the method may be performed at any other positions along the mitral annulus 40 depending on the desires of the surgeon and needs of the patient, for example.

Figure 6:
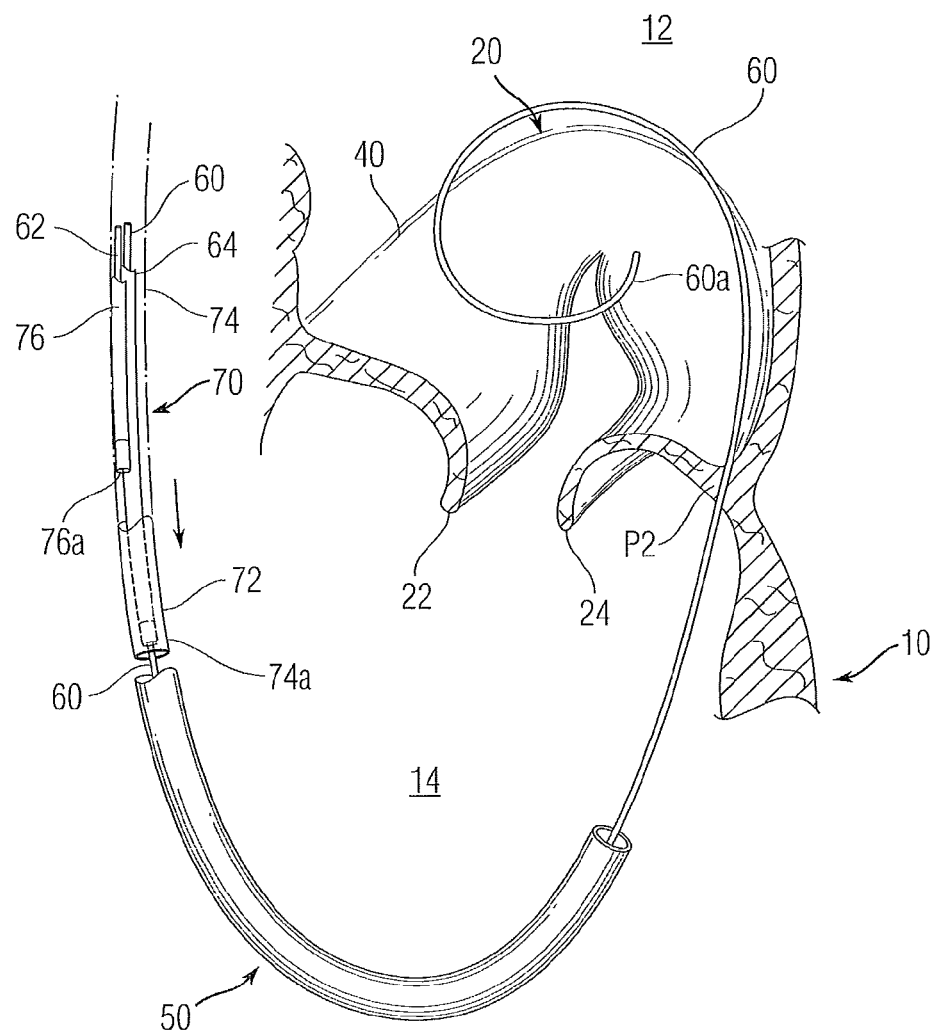
FIG. 6 is an enlarged view of the mitral valve in cross section and showing the introduction of an expandable triple lumen catheter into the left ventricle.

Catheter member 76 includes lumen 76a from which the P1 guide wire 62 may be directed. Like the P2 guide wire 60, the P1 guide wire 62 may include a RF or radiofrequency energy delivery tip 62a for assisting with penetration through the annulus tissue 40. It will be appreciated that when the "annulus tissue" is referred to herein, this refers to tissue generally along the annulus 40 and may, in fact, be tissue on the base of the posterior leaflet 24 itself. The RF guide wire 62 is inserted through the annulus tissue 40 such that distal portions thereof extend into the left atrium 12 in manners similar to RF guide wire 60 as generally shown in FIG. 6. The double lumen catheter 70, including the sheath 72, is then removed from the guide catheter 50.

Additional details concerning guide wire catheters and the procedure discussed above are set forth in commonly owned U.S. patent application Ser. No. 11/685,240, (published as U.S. patent publication No. 2008/0228265), which is hereby incorporated by reference in its entirety.

It will be understood that FIGS. 1-9 are not limiting of the present invention and merely reflect one technique for inserting and positioning guide wires in predetermined, desired locations. In another embodiment, pre-operative assessments can be used to locate the guide wires in order to restore leaflet coaptation. Accordingly, other procedures and techniques can be used for introducing and positioning the guide wires.

FIGS. 10-28 illustrate a hand operated device and procedure for attaching tissue anchors (pledgets) 2000 to tissue, such as the annulus tissue 40. In particular, an anchor (pledget) delivery catheter 100 is illustrated and is configured to controllably deliver the anchor 2000. The catheter 100 is constructed to be a hand-held device and includes a flexible catheter body 110 that extends outwardly from one end of a catheter handle 200. The catheter body 110 represents an outer sheath that receives other working components of the catheter 100 including a preloaded anchor, as described herein.

In accordance with one exemplary embodiment, the flexible catheter body (outer sheath) 110 can be in the form of a rapid exchange catheter that includes a guide wire lumen to permit the catheter 100 to be fed along a guide wire, such as guide wire 2200 (FIG. 10), to the target location. When the catheter body 110 is in the form of a rapid exchange catheter, it includes not only a main lumen for receiving the suture 1150, pusher conduit 1530 and anchor 2000 but is also includes a guide wire lumen for receiving guide wire 2200. The main lumen is open at an exit port 113 that is slightly offset (in a proximal direction) from a distal end 112 of the catheter body and is open at the handle 200 to receive the suture 1150 and other working components that internally advance the anchor 2000 as described herein. The guide wire lumen is accessible at two points located along the length of the catheter body 110 at locations spaced from the distal end 112. More specifically, the guide wire lumen is accessible at an entrance port at the distal end (tip) 112 through which the guide wire is fed into the guide wire lumen and an exit port 115 through which the guide wire exits. The exit port 115 is located along the length of the rapid exchange portion of the catheter body 110 and is located closer to the handle 200 relative to the exit port 113. To initially locate the catheter in place, the respective guide wire is inserted into the entrance port at the distal end 112 and passes through the guide wire lumen before exiting through the exit port 115. This permits the catheter 100 to be fed along the guide wire so as to locate the distal end 112 and the exit port 113 at the target location. It will therefore be appreciated that along a length of the catheter body 110 (within the rapid exchange portion), the guide wire lumen and main lumen exist in a spaced side-by-side orientation.

The catheter handle 200 includes a number of working components that are contained within a housing 210 and can be manipulated by a user to both initially deploy the anchor 2000 and place the anchor under tension to ensure proper deployment and securing of the anchor to the tissue. The housing 210 includes a first housing body 220 that has a first end 222 (front end), an opposing second end 224 (rear end), a top 226, and an opposing bottom 228. The first housing body 220 includes a base wall 223 and a peripheral wall 221 that extends outwardly from the base wall 223 and about the periphery of the base wall 223 including the ends 222, 224 and the top and bottom 226, 228 so as to define an inner compartment or space 230 (defined between the peripheral wall 221) for receiving other components as described below. The shapes of the ends 222, 224 of the housing 210 are different and similarly, the shapes of the top and bottom 226, 228 of the housing 210 are different. In particular, the top 226 includes an arcuate shaped section 227 that is generally centrally located between the ends 222, 224. Within the arcuate shaped section 227, the peripheral wall 221 includes a slot 229 that is open along the one edge of the peripheral wall 221.

The base wall 223 of the first housing body 220 includes an inner surface 232 that in part defines the inner compartment 230 and an opposing outer surface 234 that defines an exterior surface of the handle 200. A through hole 240 is formed through the base wall 223 of the first housing body 220 and is located proximate the arcuate shaped section 227. A plurality of coupling members 250 is also formed along the base surface 223 of the first housing body 220 for coupling the different parts that form the housing 210. For example, the coupling members 250 can be in the form of integral bosses that are formed at different locations along the base surface 223. For example, one boss 250 can be formed near end 222, another boss 250 can be formed near end 224, and another boss 250 can be formed along the top 226. As described below, the bosses 250 are used to securely attach the individual parts of the housing 210 together.

The first housing body 220 also includes a raised guide track 260 that is formed along the inner surface 232. The raised track 260 is an elongate structure that has two opposing closed ends 262, 264 with one end 262 being close to the through hole 240 and the other end 264 being close to the end 222 of the first housing body 220. In the illustrated embodiment, the guide track 260 has an elongate oblong shape defined by an upstanding wall and includes rounded ends 262, 264. The height of the upstanding wall is less than the height of the walls along the ends 222, 224 and sides 226, 228 of the first housing body 220.

The inner surface 232 of the first housing body 220 also includes a spool locating and retention member 290 that is integrally formed with the inner surface 232. In the illustrated embodiment, the member 290 is in the form of a structure that resembles a crosshair or the like. The member 290 is located below the slot 229.

The housing 210 includes a second housing body 300 that is complementary to the lower body 220 and is shaped and constructed to mate therewith. The second housing body 300 thus is in the form of an elongate structure having a first end 302 (front end), an opposing second end 304 (rear end), a top 306, and an opposing bottom 308. The second housing body 300 includes a base wall 305 and a peripheral wall 311 that extends outwardly from the base wall 305 along the periphery of the base wall 305 including the ends 302, 304, and top 306 and bottom 308.

Each of the ends 302, 304 and top and bottom 306, 308 includes a side wall such that the second housing body 300 has an inner compartment or space 310 for receiving other components as described below. The shapes of the ends 302, 304 are different and similarly, the shapes of the sides 306, 308 are different. In particular, the top 306 includes an arcuate shaped section 307 that is generally centrally located between the ends 302, 304. Within the arcuate shaped section 307, the peripheral wall 311 includes a slot 309 that is open along the top edge of the wall 311.

The second housing body 300 also includes an inner surface 320 that defines a floor of the inner compartment 310 and an opposing outer surface 322 that defines an exterior surface of the handle 200. The second housing body 300 includes an opening 330 that extends through the inner surface 320. In the illustrated embodiment, the opening 330 has a circular shape. The opening 330 is located proximate the slot 309. Along the bottom 308, the peripheral wall 311 has a cut out or notch 340 that extends along a length thereof. In the illustrated embodiment, the notch 340 is generally rectangular in shape.

The exterior surface 322 of the second housing body 300 is not a planar structure but instead has several recessed areas. In particular, the second housing body 300 includes a first recessed area 341 where the cut out 340 is formed and a second recessed area 343 that is adjacent and opens into a portion of the first recessed area 341 and is intended to receive a thumb of a user's hand as described herein. In addition, the exterior surface 322 also includes a third recessed area 370 that is formed along the top 306 of the second housing body 300 and includes the slot 309. The third recessed area 370 extends to the second end (rear end) 304 of the second housing body 300. A raised circular wall 380 defines the central opening 330 and is formed such that it extends into both the second and third recessed areas 343 and 370. A pair of posts 385 extends outwardly from the raised circular wall 380 into the slot 309. The pair of posts 385 is spaced apart from one another. The raised circular wall 380 is not a continuous, uninterrupted surface but instead includes a break that defines a slot that provides an entrance into the opening 330.

Within the third recessed area 370, a coupling member 381 is formed. In the illustrated embodiment, the coupling member 381 is in the form of a locking boss that includes a pair of locking tabs.

A plurality of coupling members 350 is also formed along the inner surface of the second housing body 300 for coupling the first and second housing bodies 220, 300 together to form the housing 210. For example, the coupling members 350 can be in the form of integral bosses that are formed at different locations along the inner surface and in particular, the coupling members 350 are formed at locations that complement the coupling members 250 of the first housing body 220 so that when the two housing bodies 220, 300 are mated together, the coupling members 250, 350 axially align with one another. The bosses 250, 350 are used to securely attach the housing 210 together. For example, fasteners (screws) 291 can be received into the aligned coupling member 250, 350 for attaching the first and second housing bodies 220, 300.

It will be appreciated that the first and second housing bodies 220, 300 are partially hollow members, defined by inner spaces 230, 310, and therefore, when the bodies 220, 300 are mated together, an inner compartment is formed between the first and second housing bodies 220, 300 for receiving and containing various working components of the device.

The housing 210 including the first and second housing bodies 220, 300 can be formed of any number of different materials, including a plastic material.

The catheter handle 200 has a spool assembly, as described below, and includes a spool cover 400 that at least partially covers some of the spool components and is fixedly attached to the second housing body 300. The spool cover 400 includes a first end 402 (front end) and a second end 404 (rear end), a top 406 and a bottom 408. The second end 404 of the spool cover 400 aligns and is located at the second ends 224, 304 of both the first and second housing bodies 220, 300. The spool cover 400 also includes an inner surface 411 (that faces the second housing body 300) and an opposite outer surface (exterior surface) 420. The top 406 of the spool cover 400 includes a slot 410 that axially aligns with the slots 229, 307 formed in the tops 226, 306 of the first and second housing bodies 220, 300 respectively. The bottom 408 also includes a slot 415 that cooperates with and forms an entrance into the second recessed area 343, with an arcuate wall 419 being formed along the inner surface 411 and in part defining the slot 415. The slot 410 is also defined in part by the arcuate wall 419. The arcuate wall 419 defines an arcuate shaped space or compartment 421 for receiving spool components as discussed below.

The inner surface 411 of the spool cover 400 also includes one or more coupling members to assist in locating and attaching the spool cover 400 to the second housing body 300. For example, a boss 430 can be formed along the inner surface 411 that is configured to mate with the coupling member 380 and includes complementary locking tabs that mate with the pair of locking tabs that are part of the coupling member 380. It will be appreciated that other coupling features, such locking tabs, etc., can be provided as part of the spool cover 400 to permit the spool cover 400 to be securely, yet removably, attached to the second housing body 300.

The spool cover 400 can be formed of any number of different materials, including a plastic material.

Figure 10:
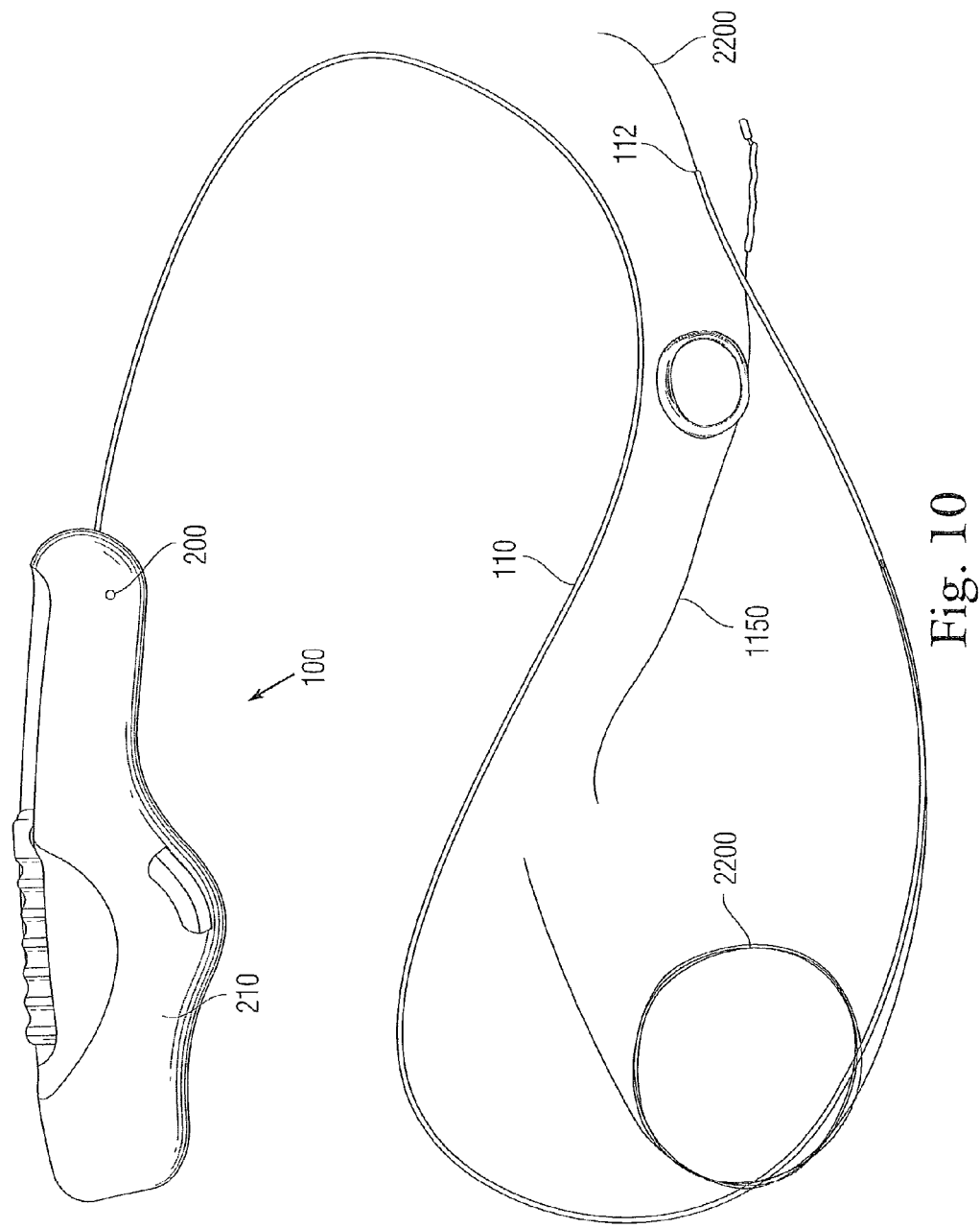
FIG. 10 is a perspective side view of an anchor (pledget) delivery catheter according to one embodiment.
Figure 16:
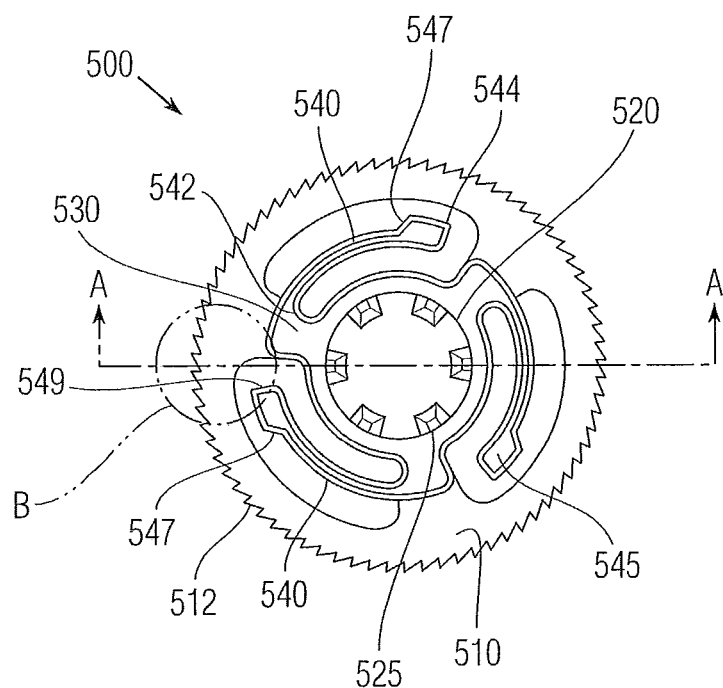
FIG. 16 is a bottom plan view of a spool ratchet of the catheter of FIG. 10.
Figure 17:
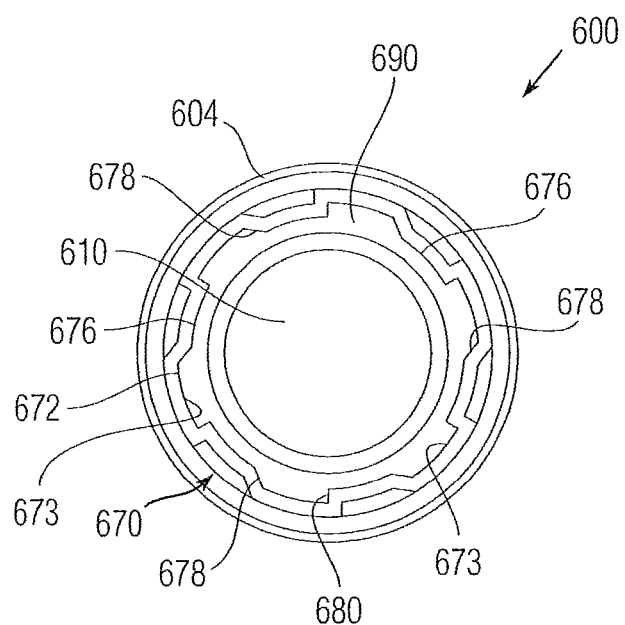
FIG. 17 is a bottom plan view of a spool of the catheter of FIG. 10.

As shown in FIGS. 10 and 16, the spool assembly that includes a spool ratchet 500. The ratchet 500 includes a lower toothed wheel 510 that has teeth 512 formed circumferentially along the peripheral edge of the wheel 510. The wheel 510 has a center hub 520 with spoke members 530 extending between the hub 520 and an inner surface of the wheel 510. The hub 520 is dimensioned and shaped so that the member 290 is received within the inner space of the hub 520 so as to locate and limit the movement (e.g., in a transverse direction) of the spool ratchet 500 while permitting rotation of the spool ratchet 500 about the member 290. The spool ratchet 500 is thus rotatably supported on the member 290 such that the spool ratchet is spaced from the inner surface of the first housing body 220. The hub 520 has a height that is greater than the wheel 510 and therefore, a portion of the hub 520 extends above the wheel 510.

In the illustrated embodiment, there are three spoke members 530. The spool ratchet 500 also includes a clutch portion that is integral to the hub 520. The clutch portion includes a plurality of flexible locking fingers 540 that extend outwardly from and are spaced from the hub 520. Each flexible finger 540 has an arcuate shape that has a first end 542 and an opposing second end 544. The first end 542 of the finger 540 is attached to the hub 520, while the second end 544 is a free end. In the illustrated embodiment, there are three flexible fingers 540 that are spaced circumferentially about the hub 520. The first end 542 of each finger 540 is attached to the hub 520 at a location where one spoke member 530 is located. A majority of the length of the finger 540 is located above a space that is formed between two adjacent spoke members 530.

The free second end 544 has a detent 545 formed thereat. The detent 545 has a first beveled edge 547 and a second edge 549 at the free second end 544. The finger 540 has a degree of flexion in a direction toward the hub 520 when a force is applied thereto resulting in the finger 540 flexing inwardly toward the hub 520. The flexing of the finger 540 results in the finger 540 storing energy. It will be appreciated that when the force is removed, the finger 540 returns to its natural state.

Along an inner surface of the hub 520, a plurality of ribs 525 are formed and are spaced circumerentially about the inner surface. The ribs 525 do not extend the entire length of the hub 520 but instead extend only a partial length thereof such that when the spool ratchet 500 is inserted onto the member 290, the ribs 525 are spaced from the member 290 and therefore, the ratchet 500 can freely rotate about the member 290 without interference between the ribs 525. The ribs 525 are thus located in the portion of the hub 520 that extends above the wheel 510.

The height of the ratchet 500 is such that when the first and second housing bodies 220, 300 are mated together, the ratchet 500 extends into the central opening 330 formed in the second housing body 300 with the clutch portion 530 is located between the raised circular wall 380. When the spool cover 400 is attached to the second housing body 300, the spool cover 400 partially covers the spool assembly.

The spool assembly also includes a spool 600. The spool 600 is designed to mate with the spool ratchet 500. The spool 600 is an annular shaped member with a central opening or bore 610. The spool 600 has a first end 602 and an opposing second end 604. The spool 600 has a first flange 630 that extends outwardly from a cylindrically shaped main spool body 620 and a second flange 640 that extends outwardly from the main spool body 620 and is spaced from the first flange 630 to define an area that receives a member to be wound about the main spool body 620.

At and proximate the first end 602, there is an annular shaped space 660 formed between the main spool body 620 and the first flange 630.

The second end 604 of the spool 600 has a clutch structure 670. The clutch structure 670 is formed by a continuous raised wall 672 that extends about the second end 604 and includes a surface that faces into the bore 610. The wall 672 is defined by an alternating pattern of recessed sections 673 that are located between platforms 676. The platforms 676 extend into the bore 610 of the spool 600. Each recessed section 674 is joined to a platform 676 by a beveled edge 678 and an edge 680 that is generally straight in nature in that the edge 680 is at least generally perpendicular to the platform 676 and the recessed section 673. The bore 610 does not have a uniform diameter from the first end to the second end but instead has a variable diameter. In particular, a ledge 690 is formed between the clutch structure 670 and a cylindrical section 692 where the bore 610 has a smaller diameter compared to the diameter in the clutch section.

The spool 600 is inserted onto the ratchet 500 with the clutch structure 670 facing inward toward the ratchet 500. The outer diameters of the first flange 630 and the second flange 640 are slightly less than the diameter of the raised circular wall 380. The spool 600 is thus securely located and rotatably held in place within the circular space between the raised circular wall 380. The second flange 640 sits on the ledge 690.

In a normal operating position (rest position), the flexible fingers 540 of the ratchet 500 are received within the clutch structure 670. More particularly, in a rest position, the detents 545 at the second ends 544 of the fingers 540 are received within the recessed areas 673 of the clutch structure 670, while the remaining portions of the fingers 540 seat against the platforms 676. In the rest position, the first beveled edge 547 of the detent 545 faces the beveled edge 678 and the second edge 549 faces the straight edge 680. The dimensions of the fingers 540 and the number and locations of the recessed areas 673 are such that when the spool 600 mates with the ratchet 500, the detents 545 of the fingers 540 are received within respective recessed areas 673. In the normal position, the spool 600 and ratchet 500 rotate in unison as a single member. As described in detail below, the clutch assembly acts as a tension limiting device and when an over-tensioning event occurs, the spool 600 and ratchet 500 slip relative to one another resulting in the detents 545 of the fingers 540 becoming temporarily disengaged from respective recessed sections 673. During the slipping motion, the catches 545 ride up along the beveled edges 678 causing the detents 545 to disengage respective sections 673 and the fingers 540 store energy as they flex inward. The displaced detents 545 ride along the adjacent platforms 676 before encountering the next adjacent recessed sections 673 (due to relative rotation between the spool 600 and ratchet 500) at which time the detents 545 are driven therein due to the fingers 540 releasing their stored energy. The clutch action is described in more detail below.

A thumb wheel 700 is coupled to the spool ratchet 500 such that rotation of the thumb wheel 700 is translated into rotation of the spool ratchet 500. The thumb wheel 700 includes a wheel portion 710 and a post 720 for coupling the thumb wheel 700 to the spool ratchet 500. The wheel portion 710 has a peripheral edge 712 that can include grip elements 714 (such as ribs) to assist a user in grasping and turning the thumb wheel 700. The post 720 is shaped to permit mating and attachment with the spool ratchet 500. For example, the post 720 includes a plurality of ribs 722 that extend circumferentially about the post 720 and can be in the form of spaced vertical ribs. The ribs 722 are received in the spaces between the ribs 525 formed along the inner surface of the hub 520. The spacing between the ribs 525 is complementary to the width of the ribs 722 such that a mechanical fit results between the thumb wheel 700 and the spool ratchet 500. The reception of the ribs 722 into the spaced between the ribs 525 effectively couples the thumb wheel 700 to the spool ratchet 500 and allows rotation of the thumb wheel 700 to be translated into rotation of the spool ratchet 500. The diameter of the wheel portion 710 is greater than a diameter of the circular wall 380 and therefore, the wheel portion 710 extends (protrudes) beyond the circular wall 380.

Figure 18:
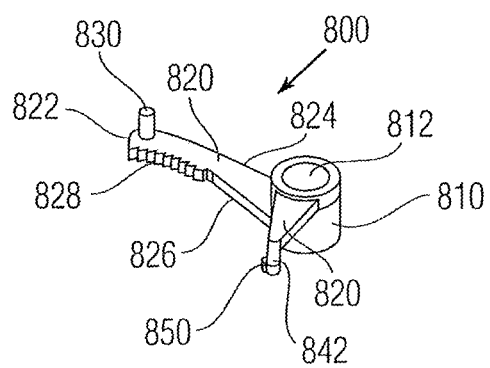
FIG. 18 is a perspective view of a spool lock of the catheter of FIG. 10
Figure 19:
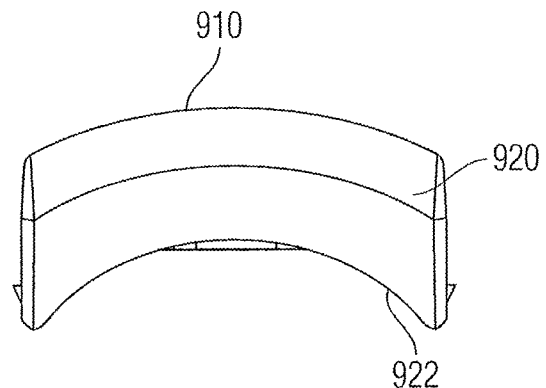
FIG. 19 is a side elevation view of a button of the catheter of FIG. 10.
Figure 20:
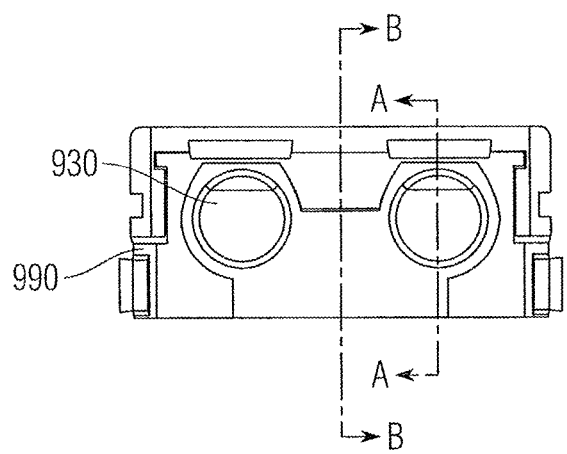
FIG. 20 is a bottom view of the button of FIG. 19.

The device 100 also includes a spool lock 800. As shown in FIG. 18, the spool lock 800 includes a main pivot body 810 that has a cylindrical shape that includes a central opening or bore 812 that extends therethrough. The central opening 812 receives a pivot to permit the spool lock 800 to pivot thereabout. In the illustrated embodiment, the pivot is in the form of bosses 250, 350 that are part of the first and second housing bodies 220, 300.

The spool lock (locking mechanism) 800 includes a first arm 820 that extends radially outward from the main pivot body 810. The first arm 820 can have a slight bend therein and has a free end 822. The first arm 820 has a first side edge (top edge) 824 and a second side edge (bottom edge) 826, with the bottom edge 826 facing the spool ratchet 500. Along the bottom edge 826 includes a toothed section defined by a plurality of teeth 828. The first arm 820 also includes a protrusion (pin) 830 that extends outwardly from the first arm 820 at or near the free end 822. In particular, the pin 830 extends outwardly from an outer face of the first arm 820, with the outer face facing the second housing body 300.

The spool lock 800 includes a second arm 840 that extends radially outward from the main pivot body 810. The second arm 840 has a free end 842. At or near the free end 842, a protrusion (pin) 850 extends outwardly from an inner face of the second arm 840. The inner face of the second arm 840 faces inward toward the first housing body 220. The length of the second arm 840 is less than the length of the first arm 820. The protrusions 830, 850 can have any number of different shapes, with the illustrated protrusions 830, 850 having a circular shape. An angle between a first axis that extends through the main pivot body 810 and the pin 830 and a second axis that extends through the main pivot body 810 and the pin 850 is about 114 degrees.

A first biasing member 860 is provided and includes a first end and a second end. The first end is attached to the pin 850, with the opposite second end being attached to a fixed protrusion (pin) 870 that is formed on the inner surface of the second housing body 300. In the illustrated embodiment, the first biasing member 860 is in the form of a spring (extension spring).

As shown in the figures, the teeth 828 are configured to mate with the teeth 512 that are formed along the peripheral edge of the lower toothed wheel 510.

A button 900 is operatively provided as part of the handle to cause controlled operation of the spool lock 800. The button 900 is a generally hollow member that includes a top wall 910 and a side wall 920 that is joined to the top wall 910. The top wall 910 has a curved shape that is complementary to the arcuate shaped sections of the first and second housing bodies 220, 300. The side wall 920 has an arcuate shaped lower edge 922. The button 900 includes an inner section that includes a coupling member 930 for movably coupling the button 900 to the second housing body 300. More specifically, the coupling member 930 is in the form of a pair of recessed sections spaced apart from one another. In the illustrated embodiment, the recessed sections 930 are in the form of circular shaped depressions (recesses).

The button 900 is coupled to the second housing body 300 by placing a pair of biasing members 950 over the posts 385 and then inserting the posts 385 into the circular shaped depressions 930. The button 900 is inserted into the slot 309 formed in the second housing body 300 and is additionally coupled to the slot 309 using additional means including inserting guide tracks 980 that are formed in side walls that define the slot 309 of the housing body 300 into complementary slots 990 formed in ends of the button 900. The button 900 thus slidingly travels within the slot 309 of the second housing body 300.

The button 900 is also formed to have a receiving space or interior that is open along a bottom thereof and is located behind the coupling members 930. The pin 830 formed along the first arm 820 is received within the receiving space. It will be appreciated that the sliding movement of the button 900 causes pivoting of the first arm 820 toward the spool ratchet 500. More specifically, movement of the button 900 toward the spool ratchet 500 causes the first arm 820 to pivot inwardly toward the spool ratchet 500 and continued movement of the button 900 results in the teeth 828 mating with the teeth 512 that are formed along the peripheral edge of the lower toothed wheel 510. In the position where the teeth 828 engage the teeth 512, the first biasing member 860 stores energy due to the pivoting movement of the second arm 840 and therefore, when the user released the button 900, the stored energy is released causing pivoting of the spool lock 800 and a return of the button 900 to a normal, rest (released) position.

It will be appreciated that the spool lock 800 serves to controllably constrain the rotation of the spool ratchet 500. In other words, when the user wishes to prevent rotation of the spool ratchet 500 and consequently, prevent rotation of the thumb wheel 700, and spool 600, the user simply presses the button 900 until teeth 828 engage teeth 512.

Figure 21:
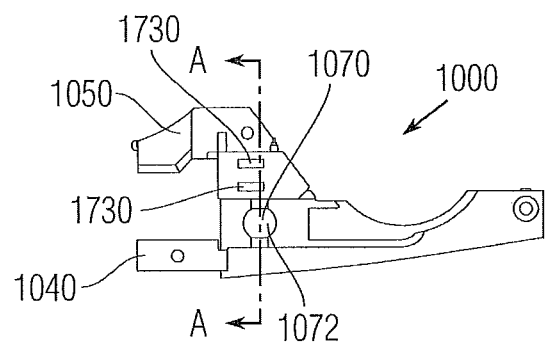
FIG. 21 is a first side of an intermediate body part of the housing of the catheter of FIG. 10.
Figure 22:
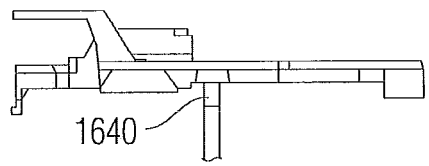
FIG. 22 is a second side of an intermediate body part of the housing of the catheter of FIG. 10.
Figure 22:
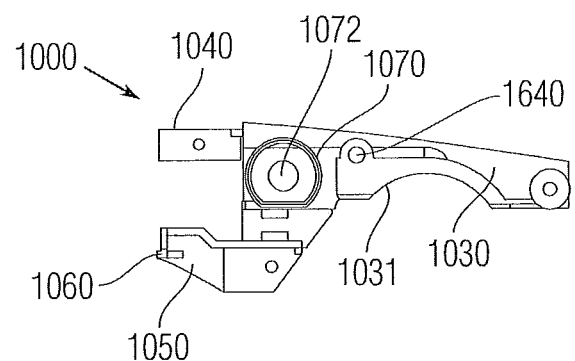

The device 100 also includes an intermediate body part 1000 that is disposed between the second housing body 300 and provides a support structure for other parts. As shown in FIG. 21, the intermediate body part 1000 is fixedly attached to the second housing body 300 using fasteners or the like. More specifically, the intermediate body part 1000 includes a first end 1010 that is attached to the second housing body 300 at a first location closer to the bottom edge of the second housing body 300 and a second end 1020 that is attached to the second housing body 300 at a second location closer to the top edge thereof.

The intermediate body part 1000 includes a main body 1030 that extends to the first end 1010. The main body 1030 includes an arcuate edge 1031. The intermediate body part 1000 also includes first and second arms 1040, 1050 that extend outwardly from the main body 1030. The first arm 1040 represents a fastening tab and includes an opening that receives a fastener for coupling the intermediate body part 1000 to the second housing body 300. The second arm 1050 includes an upstanding post 1060 at an edge thereof. The post 1060 is perpendicular to the surface of the second arm 1050. Between the arms 1040, 1050, a support surface 1070 is provided and receives a gasket member 1100. The support surface 1070 includes a through opening 1072 formed therein.

The gasket member 1100 is an at least partially hollow member that has a first end and an opposing second end with a through opening or bore 1110 extending therethrough from the first end and the second end. The gasket member 1100 has a generally cylindrical body that extends between the two ends. Between the two ends, the gasket member 1100 includes a side protrusion or post 1120 that extends outwardly from the main cylindrical body. A bore is formed through the post 1120 and is in communication with the through opening 1110 that is formed in the main cylindrical body.

The gasket member 1100 is disposed on the support surface 1070 such that the post 1120 is axially aligned with and extends through the opening 1072 formed in the support surface 1070. The gasket member 1100 can be securely coupled to the main support surface 1070 using conventional techniques including using a mechanical attachment. When attached to the main body 1030 of the intermediate body part 1000, the gasket member is generally disposed such that an axis extending through the bore 1110 extends along a length of the main body 1030 as measured from the first end to the second end thereof. As described below, the bore 1110 is constructed to receive a length of suture 1150 such that the suture extends through the bore 1110 and is wound about the spool body 620 of the spool 600. As the spool 600 is rotated in a first direction under action of the thumb wheel 700, the suture 1150 is wound around the spool 600. As described below, the suture 1150 is controllably routed within the housing 210 from the gasket member 1100 to an outlet port/opening formed at the forward end of the housing 210.

Figure 23:
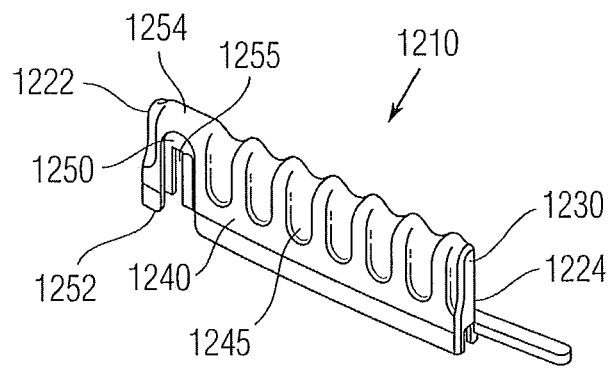
FIG. 23 is a perspective view of thumb pusher of the housing of the catheter of FIG. 10.
Figure 24:
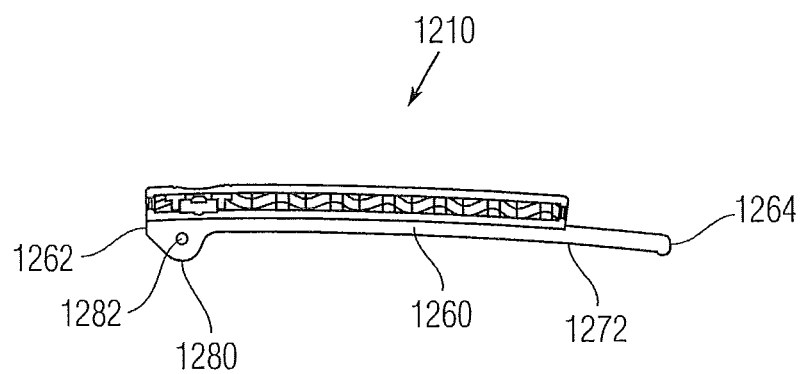
FIG. 24 is a bottom view of the thumb pusher of FIG. 23.
Figure 25:
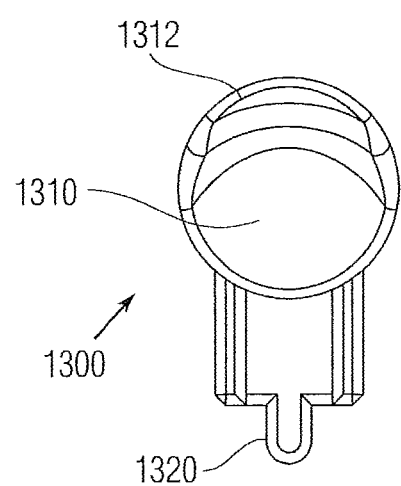
FIG. 25 is a side elevation view of a thumb pusher button.

The device 100 also includes a controllable pusher assembly, generally indicated at 1200 in FIGS. 11 and 23, that causes advancement of an anchor (pledget) as described below. The pusher assembly 1200 includes a thumb pusher (slideable pusher actuator) 1210 which can be driven to cause actuation of the pusher assembly 1200. The thumb pusher 1210 rides along a pair of raised rails 1230 that is formed on the inner surface of the first housing body 220. The thumb pusher 1210 includes a main body 1220 that has a first end 1222, an opposing second end 1224, an inner surface 1231 and an outer surface 1240 that represents an exterior surface of the thumb pusher 1210 that is engaged by the user.

While, the inner surface 1231 is generally planar in nature, the outer surface 1240 is contoured to permit the user to grip and manipulate the thumb pusher 1210. For example, the outer surface 1240 can have a plurality of recessed grip sections 1245 that provide a gripping surface for the user. The illustrated recessed grip sections 1245 are arranged parallel to one another and extend along a length of the outer surface 1240. At or near the first end 1222, a locking recess 1250 is formed in the outer surface 1240. The locking recess 1250 is open along a first edge 1252 of the outer surface 1240, while in the illustrated embodiment, the recessed grip sections 1245 are open along an opposite second edge 1254. Within the locking recess 1250, there is a guide slot or track 1255.

The thumb pusher 1210 includes an elongate locking rail 1260 that includes a first end 1262 and a second end 1264. The locking rail 1260 is formed along the inner surface 1230 and extends the length of the main body 1220 with the second end 1264 thereof protruding beyond the second end 1224. The locking rail 1260 is formed at the first edge 1252. The illustrated locking rail 1260 is in the form of a thin rectangular rail that has a locking edge formed of a plurality of teeth 1272. The first end 1262 of the rail 1260 includes a coupling section 1280 that represents a section of the rail 1260 that has increased dimensions (e.g., increased width). The coupling section 1280 can be a web portion that has a curved exposed edge and includes a through opening 1282 formed therethrough.

The first edge 1252 includes a guide slot 1280 that is formed the length of the main body 1220. The guide slot 1280 is open and shaped to receive the raised rail 1230 that is formed as part of the first housing body 220. This coupling permits the thumb pusher 1210 to ride within the housing in a controlled manner.

The thumb pusher 1210 is disposed along a bottom of the housing 210 and in particular, the thumb pusher 1210 rides within the first recessed section 341 of the second housing body 300. It will be appreciated that the main body 1220 has a slightly curved shape along its length in order to have a complementary shape and to ride along the raised rail 1230 of the first housing body 220 which has a slightly curved shape as well. The raised rail 1230 is accessible through the notch 340 formed in the first recessed section 341 of the second housing body 300.

The pusher assembly 1200 also includes a thumb pusher button 1300 that is movably disposed and contained within the locking recess 1250. The thumb pusher button 1300 includes a main thumb portion 1310 that can have a contoured surface including a lip 1312 that is complementary to the user's thumb so as to permit the user to move the thumb pusher button 1300 in a direction toward the second edge 1254. The diameter of the thumb portion 1310 is such that it is only slightly less than a width of the locking recess 1250 so that it can smoothly ride therein. The thumb portion 1310 is formed at one end of the thumb pusher button 1310, while at an opposite end, the thumb pusher button 1310 includes a locking pin 1320. The illustrated locking pin 1320 is in the form of a cylindrical shaped pin. The width of the pusher button 1310 progressively becomes smaller in the direction toward the locking pin 1320.

The thumb pusher button 1310 is biased within the locking recess 1250 by means of a biasing member 1330. The biasing member 1330 can be in the form of a compression spring. The thumb pusher button 1310 is biased against the raised rail 1230. The raised rail 1230 includes a first locking slot 1257 formed within the guide track 1255 and a second locking slot 1257 formed within the raised rail 1230. The first locking slot 1257 is located closer to the first end of the housing, while the second locking slot 1259 is located closer to the second end of the housing. The first and second locking slots 1257, 1259 can be thought of as being notches formed in the raised rail 1230.

Figure 11:
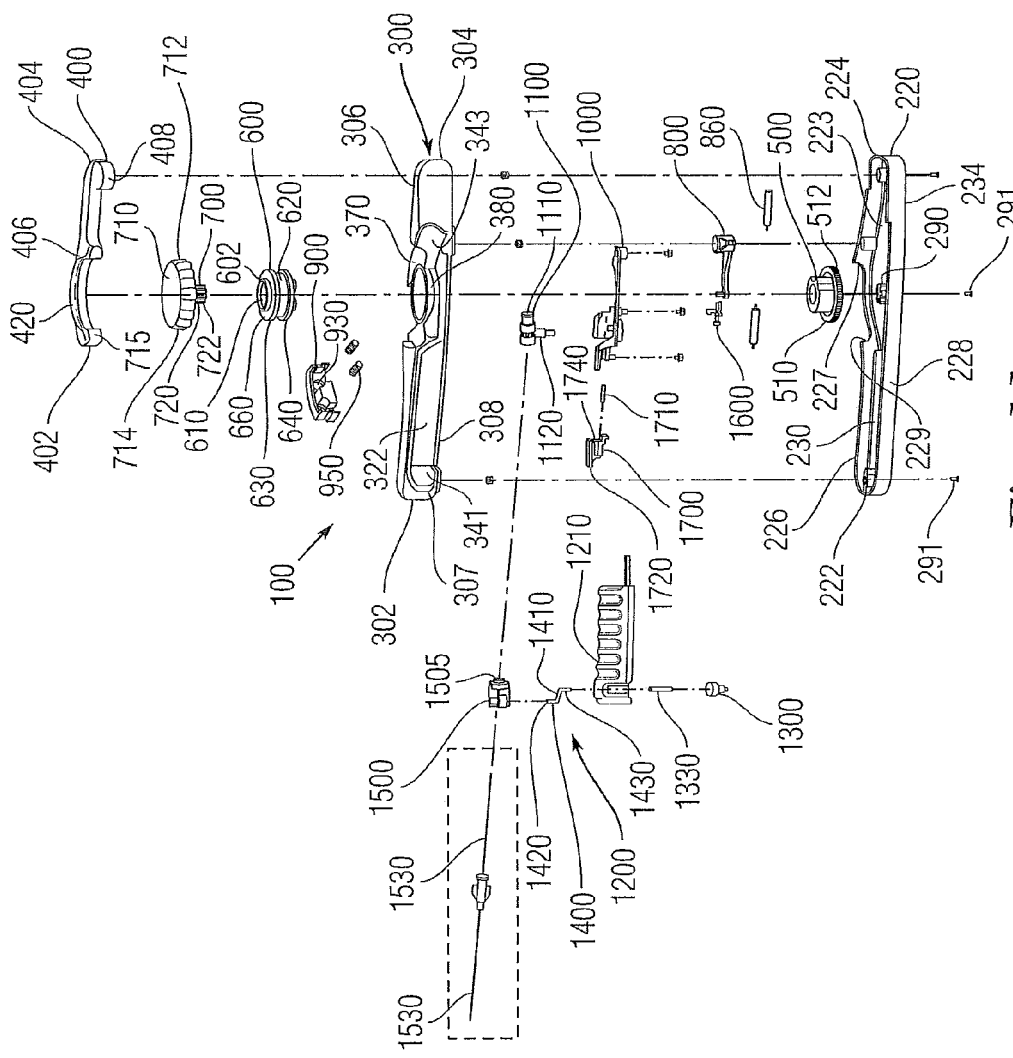
FIG. 11 is an exploded perspective view of the anchor delivery catheter of FIG. 10.
Figure 12:
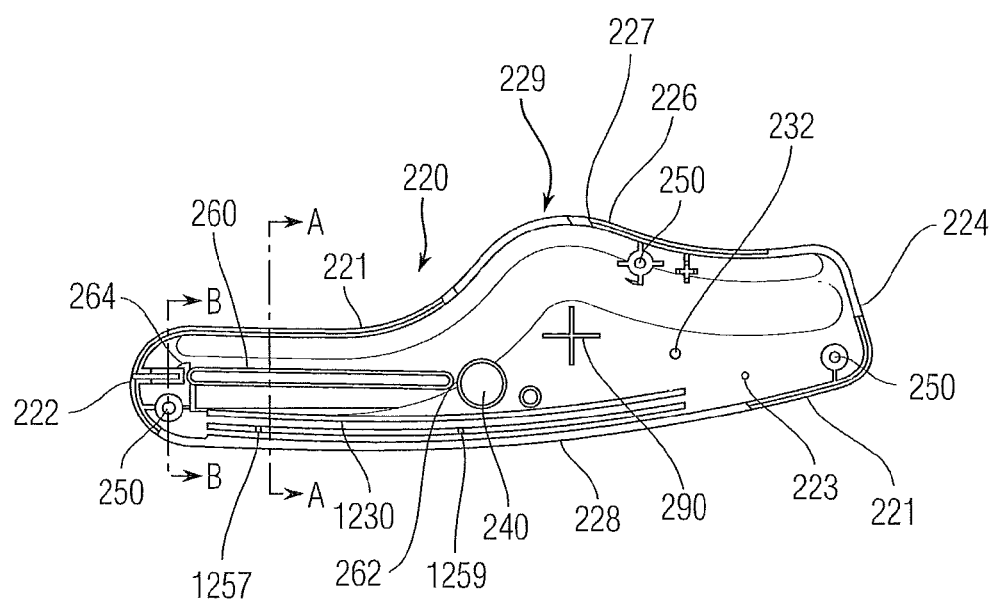
FIG. 12 is a side elevation view of a lower body part of a housing of the catheter of FIG. 10.
Figure 13:
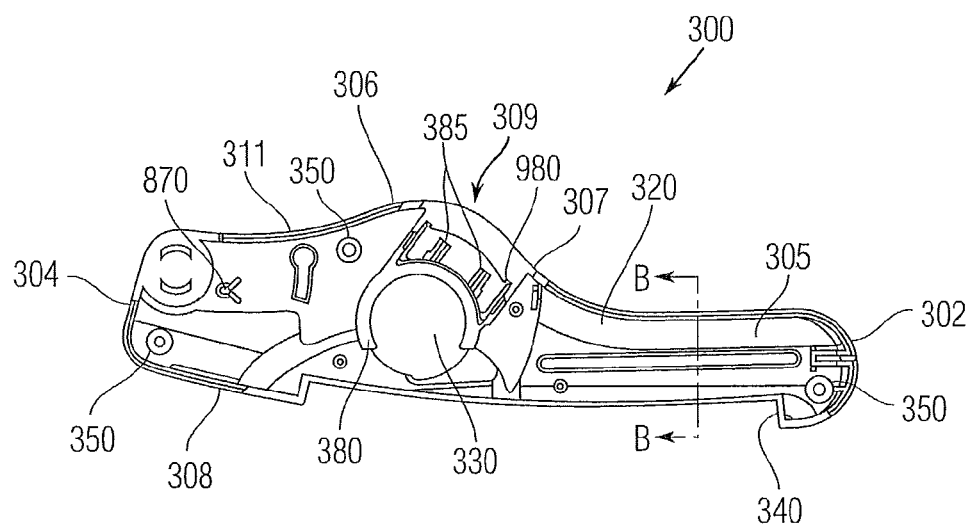
FIG. 13 is a first side elevation view of an upper body part of a housing of the catheter of FIG. 10.
Figure 14:
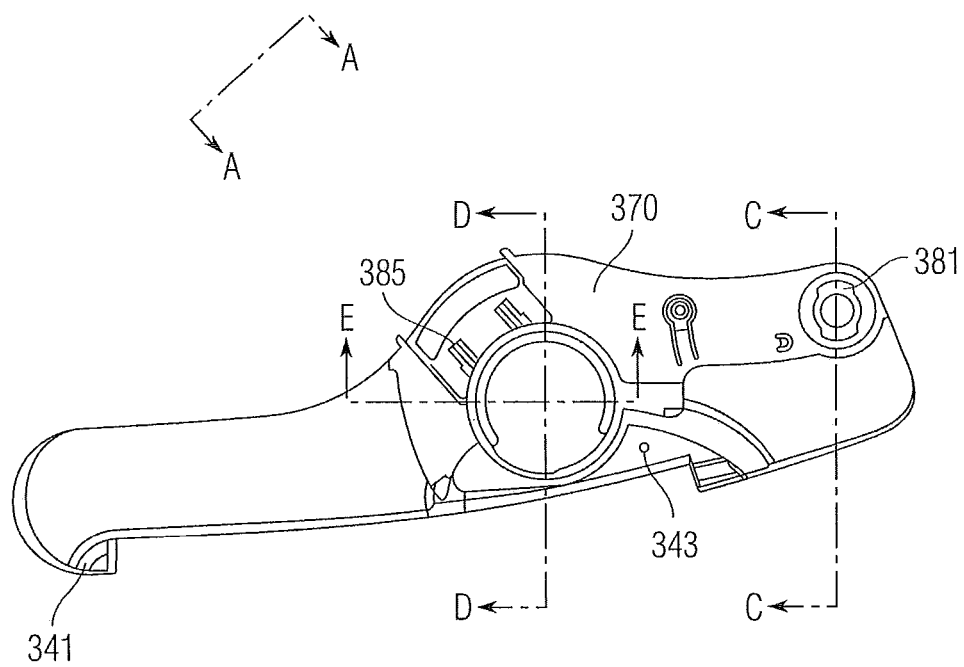
FIG. 14 is a second side elevation view of an upper body part of a housing of the catheter of FIG. 10.
Figure 15:
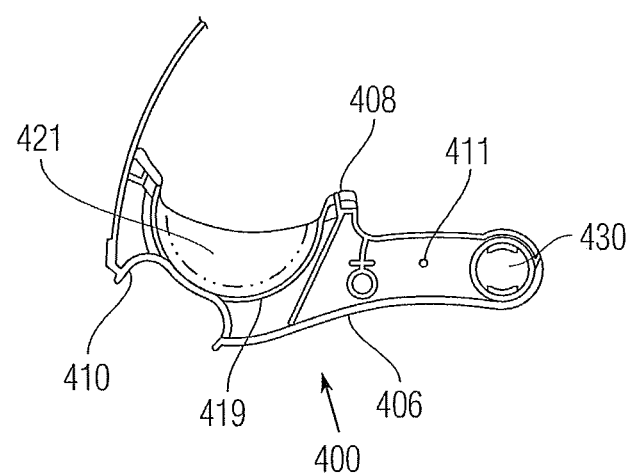
FIG. 15 is side elevation view of a spool cover of the housing of the catheter of FIG. 10.

As shown in FIGS. 11-12, the dimensions of the locking slots 1257, 1259 are selected in view of the dimensions of the locking pin 1320 and in particular, the width of the slots 1257, 1259 is slightly greater than a width (diameter) of the locking pin 1320 to permit reception of the locking pin 1320 within one of the slots 1257, 1259 when the locking pin 1320 is axially aligned therewith.

The biasing force of the biasing member 1330 causes the thumb pusher button 1310 to be biased against the raised rail 1230. Accordingly, as the thumb pusher 1210 rides along the raised rail 1230, the locking pin 1320 is biased against the raised rail 1230 and therefore, when the thumb pusher 1210 is in a position along the raised rail 1230 where the locking pin 1320 is axially aligned with one of the slots 1257, 1259, the biasing force of the biasing member 1330 causes the locking pin 1320 to be driven into the respective slot 1257, 1259, thereby locking the position of the thumb pusher 1210 and preventing the thumb pusher 1210 from continued longitudinal movement along the raised rail 1230. The importance of the locking slots 1257, 1259 is discussed herein.

The controllable pusher assembly 1200 also includes a push link 1400. The push link 1400 is a bent, curved structure that is generally S-shaped. The push link 1400 has a first end and an opposing second end. More specifically, the push link 1400 has a center portion 1410 and a pair of end portions 1420, 1430 that are at least substantially perpendicular to the center portion 1410. The push link 1400 can be formed of any number of different materials, including a metal or a plastic material. The push link 1400 is coupled to rail 1260 by inserting the end portion 1420 into the opening 1282 formed in the coupling section 1280.

Figure 26:
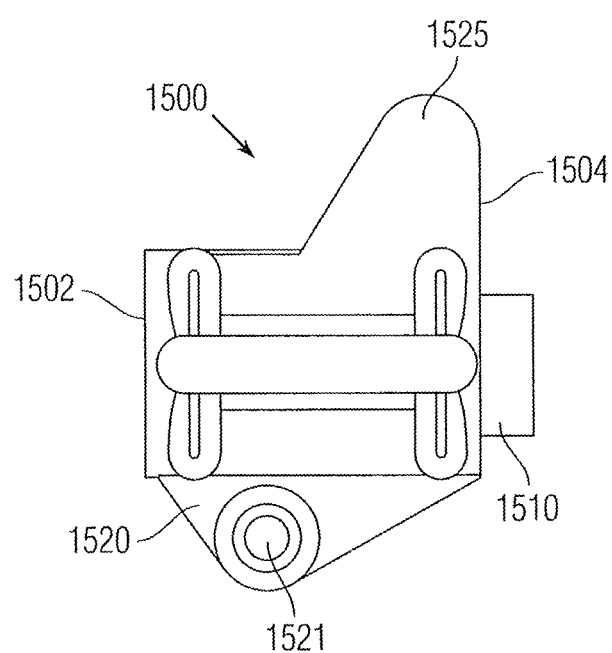
FIG. 26 is a side elevation view of a pusher.
Figure 27:
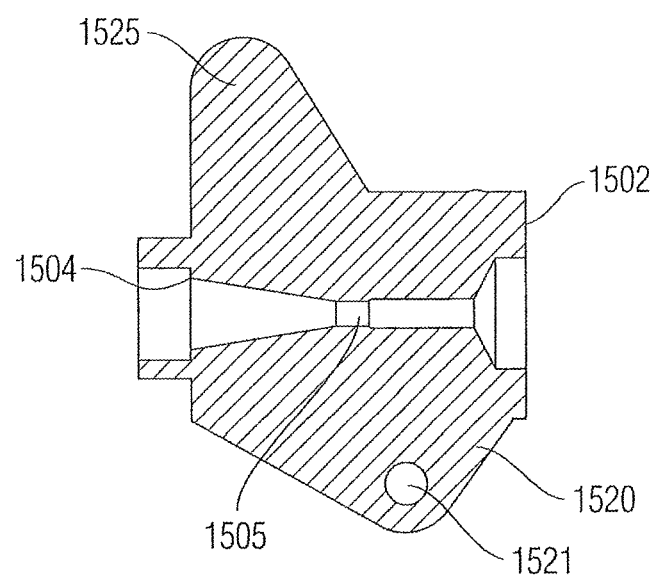
FIG. 27 is a cross-sectional view of the pusher of FIG. 26.
Figure 28:
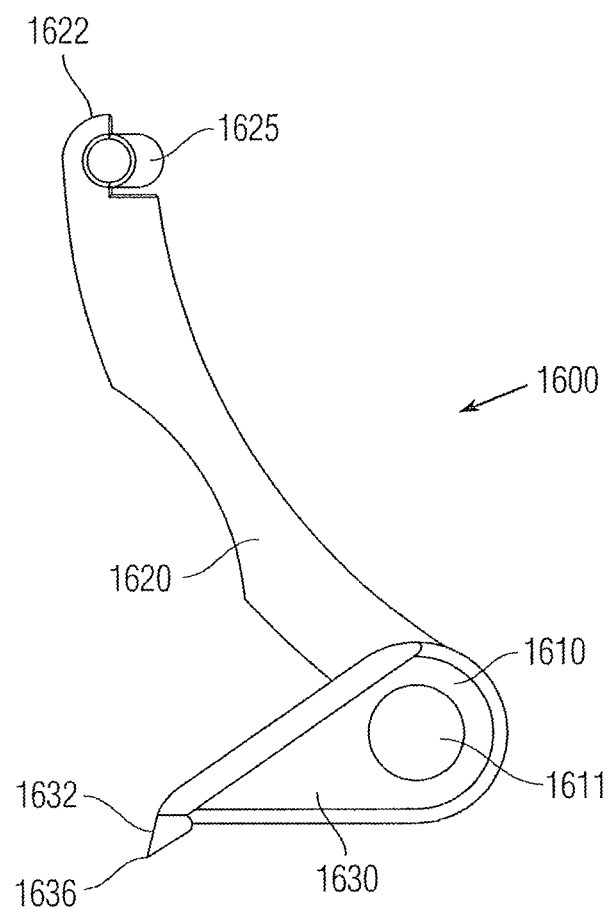
FIG. 28 is side elevation view of a push pawl.

The other end portion 1430 is coupled to a pusher 1500 (FIGS. 26 and 27). The pusher 1500 is a partially hollow part that has a first end 1502 that faces the forward end of the housing and an opposing second end 1504 that faces the spool 600. The pusher 1500 has a through hole or bore 1505 that extends therethrough from the first end 1502 to the second end 1504. The bore 1505 is formed in a main body 1510 of the pusher 1500 that has a generally cylindrical shape. A flange or wing (web) 1520 extends outwardly from the main body 1510. The flange 1520 has a through opening 1521 formed therein. The end portion 1430 of the push link 1400 is inserted into the opening formed in the flange 1520 resulting in the thumb pusher 1210 being coupled to the pusher 1500 such that the longitudinal movement of the thumb pusher 1210 is translated into longitudinal movement of the pusher 1500. The pusher 1500 also includes a second flange 1525 that has a fin shape and extends outwardly from the main body 1510.

At the first end 1502 of the pusher 1500, a pusher conduit 1530 is attached thereto and extends radially therefrom. The conduit 1530 has a lumen that receives the suture 1150 that is wound about the spool 600. More specifically, the suture 1150 is fed through the gasket member 1100 and extends to the second end 1504 of the pusher 1500 where it enters the pusher bore 1505 and travels through the pusher 1500 and exits the first end 1502 thereof into the lumen of the pusher conduit 1530. The pusher conduit 1530 can be formed of any number of different materials, including plastics and metals. In the illustrated embodiment, the pusher conduit 1530 is formed of a metal. It will be appreciated that since the pusher conduit 1530 is attached to the pusher 1500, movement of the pusher 1500 results in the pusher conduit 1530 likewise being advanced. As described herein, the pusher conduit 1530 is advanced into a lumen of a flexible outer catheter sheath 1590 and travels over the suture 1150.

As shown in the cross-sectional view of FIG. 27, the bore 1505 does not have uniform dimensions but instead, the bore 1505 has a tapered construction at the second end 1504. At the second end 1504, the bore 1505 has an inward taper to permit the suture 1150 to be more easily located and fed through the pusher 1500. The central portion of the bore 1505 has more uniform dimensions.

The operation of the pusher 1500 is described in detail below.

The controllable pusher assembly 1200 also includes a push pawl 1600. The push pawl 1600. The push pawl 1600 has a main cylindrical shaped body 1610 that defines a pivot point. The main body 1610 has an opening 1611 formed therein that defines the pivot axis of the push pawl. The push pawl 1600 has a first arm 1620 that extends outwardly from the main body 1610 and a second arm 1630 that extends outwardly from the main body 1610. The first arm 1620 terminates at an end 1622 that includes a catch or hook 1625. The second arm 1630 terminates at end 1632 that includes a pawl 1636. As shown in the figures, the first arm 1620 has a greater length than the second arm 1610.

The push pawl 1600 is pivotably disposed within the housing by inserting a pin 1640 that is an integral part of the intermediate body part 1000 into the opening 1611, thereby permitting the push pawl 1600 to rotate about the pin 1640. The push pawl 1600 is positioned such that the first arm 1620 faces the button 900 and the second arm 1630 faces the locking rail 1260.

A biasing member 1650 is attached at one end to the hook 1625 and is attached at its other end to the upstanding post 1060 so as to subject the push pawl 1600 to a biasing force. The pawl 1636 of the push pawl 1600 interlockingly engages the teeth 1272 formed along the locking edge 1270 of the locking rail 1260. As the thumb pusher 1210 is moved along the raised rail 1230 of the first housing body 220, the pawl 1636 successively engages the teeth 1272. As described in more detail below, the push pawl 1600 is designed to prevent uncontrolled rearward movement of the thumb pusher 1210 and thereby prevents undesired movement of the suture.

The controllable pusher assembly 1200 also includes a spool detent (locking mechanism) 1700. The spool detent 1700 is coupled to the intermediate body part 1000 in a biased manner and such that the spool detent slidingly moves relative to the fixed intermediate body part 1000. The spool detent 1700 is disposed along the support surface 1070 adjacent the opening 1072. The spool detent 1700 has a bottom rail structure 1720 that mates with a pair of locating and coupling tabs 1730 that are formed as part of the intermediate body part 1000 to allow the controlled sliding motion of the spool detent 1700.

The spool detent 1700 is biased relative to the intermediate body part 1000 by means of a spring 1710 that is disposed between the spool detent 1700 and the intermediate body part 1000. The spool detent 1700 further includes a detent section 1740 that includes a surface that has teeth formed thereat. The detent section 1740 represents an upstanding section that protrudes away from the main body of the spool detent 1700. The teeth of the detent section 1740 are complementary to and constructed to engage the teeth 512 formed circumferentially along the peripheral edge of the wheel 510 of the spool ratchet 500. The spool detent 1700 is designed so that in a normal rest position, the spring 1710 biases the spool detent 1700 away from the spool ratchet 500 such that the teeth of the spool detent 1700 do not engage the teeth 512.

When the spool detent 1700 is mated to the intermediate body part 1000, the upstanding detent section 1740 is disposed between the first arm 1620 of the push pawl 1600 and the wheel 510 of the spool ratchet 500. As the thumb pusher 1210 moves rearwardly along the raised rail 1230, the pusher 1500 similarly moved rearwardly within the housing toward the spool. The flange 1525 of the pusher 1500 contacts an end of the spool detent 1700 and continued rearward motion of the pusher 1500 causes the spool detent 1700 to move along the intermediate body part 1000. This continued motion of the pusher 1500 and movement of the pusher 1500 results in the spring 1710 storing energy. The continued rearward motion of the thumb pusher 1210 and the pusher 1500 results in the teeth of the spool detent 1700 engaging the teeth 512. Once the teeth of the spool detent 1700 engage the teeth 512 of the spool ratchet 500, the spool ratchet 500 can no longer freely rotate and thus, the spool 600 can no longer rotate. Conversely, when the thumb pusher 1210 is moved in direction away from the spool, the pusher 1500 similarly moves and the flange 1525 is free of engagement with the spool detent 1700 and the stored energy of the spring 1710 is released.

In accordance with the present invention, the anchor delivery catheter 100 includes a tensioning limiting device in the form of the spool clutch mechanism that is described above. As described below, the spool clutch mechanism is configured to ensure that the suture 1150 can not be overtightened during deployment of the suture 1150.

As previously discussed, the catheter 100 is constructed for controllably delivering an anchor (pledget) 2000. The anchor 2000 can have any number of different constructions including those constructions that are disclosed in commonly owned U.S. patent application Ser. No. 12/273,670 (published as US 2009/0076547), which is hereby incorporated by reference in its entirety.

As shown in FIGS. 29A-29E, the tissue anchor 2000 includes a tensioning member (suture 1150) that is used to activate a flexible, elongate flat strip 2100 having proximal and distal end portions 2100a, 2100b. Strip 2100 includes a tip 2106 that is formed or otherwise secured on the distal end portion 2100b. However, it will be appreciated that the tissue anchor 2000 is merely one type of tissue anchor that can be used in accordance with the instruments of the present invention. The tissue anchor 2000 is of a fan fold design; however, the tissue anchor is not limited to have such a folding type design. In particular, other types of tissue anchors can be used and in particular, another type of tissue anchor can be in the form of a tissue anchor that has sufficient surface area on an atrial side thereof and/or barbs that assist in seating the tissue anchor against the tissue. The barbs discourage pull through by seating against and intimately engaging the tissue. In this type of anchor design, the tissue anchor may not have a ventricular component at all. In yet another embodiment, the anchor can be two-pieces, one piece on the atrial side that is seated by the slip-clutch mechanism followed by a ventricular anchor to result in a plug on both sides of the tissue. In each of these embodiments, the slip clutch mechanism is configured to prevent the anchor from being pulled through the tissue.

In the fan fold type anchor design, the tensioning member 1150 and the tip 2106 are arranged such that the tensioning member 1150 slides relative to the tip 2106. More particularly, the tensioning member 1150 can be threaded through the tip 2106. Tip 2106 is made to be relatively rigid as compared to other flexible portions of strip 2100 and of smaller diameter than the width of strip 2100.

The strip 2100 may be about 40 mm long by about 3 mm wide. Of course, any other desired dimensions and shapes may be used depending on application needs. This may be desirable to achieve a lower profile deployed and fastened configuration with fewer folds that may lead to more versatile applications, lower incidents of blood clotting, easier use, etc. In addition, respective proximal and distal radiopaque bands 2120, 2122 are secured to the suture 1150 at the proximal end portion of the strip 2100 and to either the interior or exterior of the distal tip 2106. Under a fluoroscope, these bands or other markers 2120, 2122 will indicate to the surgeon that the anchor 2000 has been deployed, activated and fully compressed and/or fastened as necessary during the procedure. The tip 2106 itself may alternatively be formed from a radiopaque material. A knot 2150 formed in the suture 1150 or other tensioning member is a slip knot through which another portion of the suture 1150 slides during activation of the tissue anchor 2100. It will be appreciated that this slip knot 2150 may be replaced by another element which serves essentially the same purpose but takes the form, for example, of a small tubular element or other feature similar in function to a slip knot.

The tensioning member or suture 1150 can advantageously extend through respective fold portions 2100c of the elongate strip 2100 in essentially an hourglass configuration. Fold lines of the portions 2100c are represented at 2100d. Specifically, adjacent portions of the suture 1150 located near the proximal and distal end portions 2100a, 2100b of the strip 2100 are spaced farther apart than the adjacent portions of the suture 1150 in the middle of the strip 2100.

The tensioning member or suture 1150 may be threaded or otherwise attached along the strip 2100 in any number of manners including, for example, x-patterns or other crossing patterns, zig-zag patterns, etc. that may alter the folded or otherwise shortened or compressed footprint of the anchor into various beneficial shapes, such as flower shapes, circular shapes or other rounded shapes, ball shapes or other configurations. Modifications of the manner in which the tensioning member or suture 1150 is threaded or otherwise attached along the length of strip 2100 may result in higher or lower tensioning force being required to compress the anchor and/or higher or lower friction holding force that may help maintain the anchor in the compressed or shortened configuration.

Additional details of the anchor 2000 are described in the '670 application.

The anchor 2000 is loaded into the distal tip 112 of the catheter body 110 with the strip 2100 being in an extended position (non-compressed) condition. In this loaded position within the catheter body 110, the pusher conduit 1530 (which travels over the suture 1150) engages and contacts the loaded strip 2100 as the pusher conduit 1530 is advanced within the catheter body 110 as described herein. The continued advancement of the pusher conduit 1530 causes the distal end section of the anchor 2000 to be deployed and ejected from the tip 112 of the catheter body 110.

FIGS. 29A-29E illustrate a series of steps for deploying and securely fastening the tissue anchor 2000 to a layer of tissue 101. Generally, as shown in FIG. 29A, the combination of the elongate strip 2100 and tensioning member or suture 1150 is deployed through the layer of tissue 101. One end or portion 1150a of the suture 1150 that extends through the slip knot 2150 is then pulled. This causes the distal portion 2100b of the elongate strip 2100 to fold and compress against the distal side of the tissue layer 101. As shown in FIG. 29B, further pulling of the tensioning member 1150 causes the slip knot 2150 to ride upwardly or distally along the suture 1150 and against a proximal portion 2100a of the elongate strip 2100 thereby folding and compressing the proximal portion 2100a against the proximal side of the tissue layer 101 as shown in FIG. 29C. As shown in FIG. 29D, a suitable crimp or locking element 103 can be used to securely lock the slip knot 2150 in place relative to the suture or tensioning member segment which extends therethrough. This will lock the entire anchor 2000 in place with the respective proximal and distal folded strip portions 2100a, 2100b securely retaining the tissue layer or layers 101 therebetween. FIG. 29D shows the tip 2106 acting as a retainer on top of the distal end portion 2100b to assist in holding the distal end portion 2100b in place. FIG. 29E shows an alternative in which the tensioning member is threaded through at least one hole 2112a more centrally located in the tip. Yet another alternative would be to thread the tensioning member through two centrally located holes instead of through the proximal end of the tip 2106 and one centrally located hole 2112a as shown in FIG. 29E. These alternatives allow the tip 2106 to act more like a "T"-bar with forces acting in a more perpendicular or normal manner relative to the distal end portion 2100b of the strip 2100.

In a normal, rest (start) position, the thumb pusher 1210 is in a fully retracted position with the thumb pusher button 1300 in a locked position along the rail 1230. More specifically, the pin 1320 of the button 1300 is lockingly received within the notch 1259, thereby locking the thumb pusher 1210 in place. To deploy the anchor 2000, the pusher button 1300 is moved in a direction toward the edge 1254, overcoming the biasing force, and thereby retracting the pin 1320 from the notch 1259. This action frees the thumb pusher 1210 and permits the thumb pusher 1210 to move along the raised rail 1230 toward the front end of the handle housing 210. As the thumb pusher 1210 moves, the push pawl 1600 engages the teeth 1272 in a ratcheting manner (to prevent the thumb pusher 1210 from inadvertently moving rearward) as the thumb pusher 1210 is advanced.

Since the pusher 1500 is coupled to the thumb pusher 1210, the movement of the thumb pusher 1210 causes the pusher 1500 to likewise be driven in the same direction and since the pusher conduit 1530 is fixedly attached to the pusher 1500, the advancement of the thumb pusher 1210 causes the pusher conduit 1530 to be driven and advanced into the main lumen of the catheter body 110. The anchor 2000 is at least partially disposed in the pusher conduit 1530 (in an initial retracted state) and therefore, the advancement of the pusher conduit 1530 toward the distal end 112 of the catheter body 110 results in at least partial deployment of the anchor 2000 as described herein.

In addition, the deployment of the anchor 2000 by means of the pusher conduit 1530 causes the suture 1150 to unwind from the spool 600 due to the anchor 2000 being coupled to the suture 1150.

The thumb pusher 1210 is advanced forward until the pin 320 is axially aligned with the notch 1257 at which time, the biasing force of spring 1330 causes the pin 1320 to lock into place within the notch 1257. In this fully extended position, the thumb pusher 1210 is fully advanced within the catheter body 110. The distance between the two locking notches 1259, 1257 is selected so as to permit the pusher conduit 1530 to travel a sufficient distance within the main lumen of the catheter body 110 to not only contact the pre-loaded anchor 2000 but also deploy or eject at least a portion of the anchor 2000.

The distal tip 112 of the catheter body 110 can have a sharpened point (beveled edge) that facilitates and permits the distal tip 112 to pierce tissue, such as the annulus tissue of a mitral valve. When the catheter 100 is used part of an annuloplasty procedure on a mitral valve, the catheter body 110 is deployed over the guide wire 2200 until the distal tip 112 pierces and clears the annulus such that the exit port 113 is similarly on the same side of the annulus as the distal tip 112. Once the exit port 113 is located on an atrial side of the annulus, the thumb pusher 1210 is used to deploy a portion of the anchor 2000 on the atrial side of the annulus. The tensioning member (suture) 1150 is again used to activate the flexible, elongate flat strip 2100 having proximal and distal end portions 2100a, 2100b. The beveled distal tip 112 of the catheter body 110 and optionally, the tip 2106 help to penetrate the annulus tissue as the catheter body 110 and the elongate strip 2100 are extended through the annulus tissue. To help prevent the distal portion 2100b of the elongate strip from pulling back through the annulus tissue as the catheter body is withdrawn from the annulus tissue, the free end of the tensioning member 1150 is pulled while the distal tip 112 is still penetrated through the annulus tissue and into the left atrium from the left ventricle. This forms the distal portion 2100b into a folded or otherwise shortened configuration. The catheter body 110 can then be withdrawn without also withdrawing the elongate flexible strip 2100 with it.

As described herein, the distal portion of the elongate strip 2100 is deployed by means of actuation of the pusher 1500 and the advancement of the pusher conduit 1530 within the catheter body 110 into engagement with the anchor 2000. This action causes the distal portion of the strip 2100 to be ejected out from the distal tip 112. During and after deployment of the distal portion of the strip 2100, the suture 1150 is tensioned by first pressing the button 900 which causes the spool lock 800 to pivot and the teeth 828 of the spool lock 800 engage the teeth 512 of the spool ratchet 500. The engagement of teeth 828 to teeth 512 prevent the spool ratchet 500 from freely backspinning as the suture 1150 is tensioned.

More particularly, the suture 1150 is tensioned by rotating the thumb wheel 700 which causes rotation of both the spool 600 and the spool ratchet 500.

Use of the spool lock 800 permits one handed operation of the device. The thumb wheel 700 can be rotated, the physician's thumb can be lifted and repositioned on the wheel for further turning while lock 800 permits back spin while the thumb is not in contact with the wheel.

As the thumb wheel 700 is rotated, the suture 1150 is increasingly placed under tension; however, as previously discussed, the catheter 100 of the present invention includes a tension limiting mechanism in the form of a slip clutch assembly that prevents tissue pull through in that the assembly prevents the tissue anchor from being pulled through the tissue due to excessive tensioning. As the suture 1150 is wound and placed increasingly under more tension, the clutch assembly acts as a tension limiting device and when an overtensioning event occurs, the spool 600 and ratchet 500 slip relative to one another resulting in the detents 545 of the fingers 540 becoming temporarily disengaged from respective recessed sections 673. During the slipping motion, the catches 545 ride up along the beveled edges 678 causing the detents 545 to disengage respective sections 673 and the fingers 540 store energy as they flex inward. The displaced detents 545 ride along the adjacent platforms 676 before encountering the next adjacent recessed sections 673 (due to relative rotation between the spool 600 and ratchet 500) at which time the detents 545 are driven therein due to the fingers 540 releasing their stored energy. This slipping action can repeatedly occur depending upon the operation of the device, etc.

It will be understood that the slip clutch assembly is configured to prevent tissue pull through. In other words, the slip clutch assembly is configured to limit the force applied to an atrial anchor to prevent tissue pull through (e.g., prevent the anchor from being pulled through the tissue itself).

As the ratchet 500 slips relative to the spool 600, the user will receive auditory and/or sensory feedback that the suture 1150 is sufficiently tensioned and should not be placed under further tension so as to prevent tissue pull through. When the slip clutch assembly slips, the distal portion of the strip 2100 should already be fully compressed on one side of the tissue (annulus tissue) as shown. Once the distal portion of the strip 2100 is fully compressed, the proximal portion 2100a of the elongate strip 2100 is then deployed by retracting the distal tip 112 of the catheter body 110 by further pulling the catheter body 110 in a proximal direction, and thereby exposing the full length of strip 2100. In other words, the catheter body 110 is pulled so that it is on the other side of the annulus tissue relative to the compressed distal portion. By retracting the catheter body 110 in a proximal direction so that the distal tip 112 is spaced a distance from the annulus tissue, the proximal portion of the anchor 2100a of the elongate strip 2100 is exposed and positioned outside of the catheter body 110 to allow tensioning thereof on a ventricular side of the annulus. The spool lock 800 is disengaged during the retraction in order to permit unspooling of the suture 1150 as the catheter body 110 is pulled relative to the distal end of the strip 2100.

The tensioning member 1150 is then pulled or tensioned so as to draw and compress the proximal portion 2100a of the elongate strip 2100 into a folded, shortened condition against an underside of the annulus tissue.

This process is repeated as many times as necessary to create the necessary number of tissue plications by placing tissue anchors in different locations.

After the tissue anchors are secured to the tissue sites, additional steps can be undertaken such as those described in the '240 application.

It will be appreciated that the present invention provides a hand held and hand operated device that always a tissue anchor (pledget) to be controllably deployed and anchored to tissue. The hand operated device includes a number of safety features to ensure the anchor is properly delivered and to ensure that overtensioning of the tensioning element (suture) does not result.

While the invention has been described in connection with certain embodiments thereof, the invention is capable of being practiced in other forms and using other materials and structures. Accordingly, the invention is defined by the recitations in the claims appended hereto and equivalents thereof.

What is claimed is:

1. A tissue anchoring system comprising:
   a tissue anchor member that is configured for being anchored against tissue;
   a tensioning member operatively connected to the anchor member such that the anchor member can slide relative to the tensioning member, the tensioning member capable of being pulled to cause the anchor member to change a position thereof; and
   a hand operated deployment catheter operable to extend and deploy the anchor member therefrom, the deployment catheter having a handle and including:
   a rotatable member about which the tensioning member is routed and a clutch assembly for limiting tension within the tensioning member, wherein the rotatable member is contained within the housing;
   a deployable pusher assembly for controllably deploying a portion of the anchor member, the pusher assembly including a slideable pusher actuator that is coupled to and accessible along the handle and is moveable between a retracted position and an extended position in which the pusher assembly deploys at least a portion of the anchor member; and
   a locking mechanism that selectively engages the rotatable member and prevents rotation thereof, wherein when the slideable pusher actuator is in the retracted position, the locking mechanism automatically engages the rotatable member to prevent rotation thereof and maintain a length of the tensioning member that exists external to the rotatable member.

2. A hand operated tissue anchoring system for deploying a tissue anchor:
   an anchor member capable of being inserted through tissue and suitable for anchoring against at least one side of the tissue;
   a tensioning member operatively connected to the anchor member such that the anchor member can slide relative to the tensioning member, the tensioning member capable of being pulled to cause the anchor member to move relative to said tensioning member to apply tension thereto to seat the anchor member;
   a deployment catheter operable to extend and deploy the anchor member therefrom, the deployment catheter including:
   a handle;
   a catheter body that is fixedly attached to the handle at one end, the anchor member and connected tensioning member being contained within a main lumen of the catheter body;
   a spool assembly including a spool about which the tensioning member is routed;

a slip clutch assembly that is operatively coupled to the spool assembly, the slip clutch assembly being configured to limit tension within the tensioning member as the tensioning member is pulled and wound about the spool as tension is applied to the anchor member; and a deployable pusher assembly for controllably deploying a portion of the anchor member, the pusher assembly including a slideable pusher actuator that is coupled to and accessible along the handle and is moveable between a retracted position and an extended position in which the pusher assembly deploys at least a portion of the anchor member;

wherein the pusher assembly includes a pusher that is coupled to and movable with the slideable pusher actuator and has a pusher conduit fixedly attached and extending outwardly from one end thereof, the pusher conduit having a lumen that receives the tensioning member, and wherein the spool assembly includes a spool detent that is movable within a guide slot formed in a part that makes up a housing of the handle and includes a portion that has teeth, wherein when the slideable pusher actuator is in the retracted position, a portion of the pusher engages and drives the spool detent toward the spool assembly such that the teeth of the spool detent engage complementary teeth formed as part of the spool assembly and prevent the spool assembly from rotating.

3. The system of claim 2, wherein the anchor member is a flexible anchor member that is movable between an elongate configuration and a shortened configuration, the anchor member having a proximal end portion, a distal end portion and a compressible intermediate portion, wherein the shortened configuration comprises a zig-zag fold pattern and pulling of the tensioning member causes the anchor member to move from the elongate configuration to the shortened configuration, wherein the compressible intermediate portion can compress and thereby adjust to a thickness of the layer of the tissue between the proximal and distal end portions.

4. The system of claim 2, wherein the anchor member is formed from a material selected from at least one of: natural fibers, synthetic fibers, polymers, and metals.

5. The system of claim 2, wherein said tensioning member comprises a suture.

6. The system of claim 2, wherein the tensioning member includes a stop member engageable with the anchor member.

7. The system of claim 6, wherein said stop member further comprises a knot in the tensioning member.

8. The system of claim 2, wherein the catheter body is a rapid exchange catheter body that includes a guide wire lumen for receiving a guide wire and a main lumen for receiving the anchor member and the tensioning member.

9. The system of claim 8, wherein the guide wire lumen opens at a distal tip of the catheter body with the main lumen of the catheter body being open at a location that is spaced from and located proximal to the distal tip.

10. The system of claim 8, wherein the pusher assembly includes a pivotable push pawl that is coupled to a housing of the handle and interlockingly engages the slideable pusher actuator such that free rearward movement of the pusher assembly is prevented.

11. The system of claim 10, wherein the push pawl is coupled to a biasing member that is fixedly attached to the housing and the push pawl has an arm that has teeth that interlockingly engages teeth formed along a locking rail of the slideable pusher actuator.

12. The system of claim 10, wherein the slideable pusher moves along a rail formed along an inner surface of the housing of the handle, with the rail including a first locking notch for locking the slideable pusher in the extended position and a second locking notch for locking the slideable pusher in the retracted position.

13. The system of claim 2, wherein the spool assembly further includes a spool ratchet that includes a lower toothed wheel that has teeth formed circumferentially along a peripheral edge of the wheel, the spool ratchet having a first clutch member that is part of the clutch assembly and mates with a second clutch member that is part of the spool, wherein the spool ratchet and spool slip relative to one another when tension within the tensioning member exceeds a threshold value, thereby preventing the tensioning member from being overtensioned.

14. The system of claim 13, wherein the spool assembly further includes a rotatable thumb wheel that is accessible along the handle and is coupled to the spool ratchet such that rotation of the thumb wheel is translated into rotation of the spool ratchet.

15. The system of claim 13, wherein the first clutch member comprises at least one flexible finger that includes a locking detent at a free end thereof and the second clutch member comprises a circumferential raised wall that is formed as part of the spool and includes a plurality of recessed sections that alternate with platform sections of the raised wall, wherein in a normal operating position, the locking detent is biased into and held within one of the recessed sections until the tension within the tension member exceeds the threshold value, whereby the locking detent slips out of engagement with the recessed section and rides along an adjacent platform section until being biased into the next recessed section.

16. A hand operated tissue anchoring system for deploying a tissue anchor:

an anchor member capable of being inserted through tissue and suitable for anchoring against at least one side of the tissue;

a tensioning member operatively connected to the anchor member such that the anchor member can slide relative to the tensioning member, the tensioning member capable of being pulled to cause the anchor member to move relative to said tensioning member to apply tension thereto to seat the anchor member;

a deployment catheter operable to extend and deploy the anchor member therefrom, the deployment catheter including:

a handle;

a catheter body that is fixedly attached to the handle at one end, the anchor member and connected tensioning member being contained within a main lumen of the catheter body;

a spool assembly including a spool about which the tensioning member is routed;

a slip clutch assembly that is operatively coupled to the spool assembly, the slip clutch assembly being configured to limit tension within the tensioning member as the tensioning member is pulled and wound about the spool as tension is applied to the anchor member; and a deployable pusher assembly for controllably deploying a portion of the anchor member, the pusher assembly including a slideable pusher actuator that is coupled to and accessible along the handle and is moveable between a retracted position and an extended position in which the pusher assembly deploys at least a portion of the anchor member;

wherein the spool assembly further includes a spool ratchet that includes a lower toothed wheel that has teeth formed circumferentially along a peripheral edge of the wheel, the spool ratchet having a first clutch member that is part of the clutch assembly and mates with a second clutch member that is part of the spool, wherein the spool ratchet and spool slip relative to one another when tension within the tensioning member exceeds a threshold value, thereby preventing the tensioning member from being overtensioned; and wherein the spool assembly further includes a button that is accessible along the handle and a spool lock that is pivotably coupled to a housing of the handle and is coupled to both the button and a biasing member, the spool lock including an arm that has a locking edge that includes a plurality of teeth, wherein movement of the button toward the spool causes pivoting the arm of the spool lock toward to the spool ratchet until the teeth of the spool lock interlockingly engage the teeth of the spool ratchet, thereby preventing free rotation of the ratchet wheel and spool.

17. A hand operated tissue anchoring system for deploying a tissue anchor:

an anchor member capable of being inserted through tissue and suitable for anchoring against at least one side of the tissue;

a tensioning member operatively connected to the anchor member such that the anchor member can slide relative to the tensioning member, the tensioning member capable of being pulled to cause the anchor member to move relative to said tensioning member to apply tension thereto to seat the anchor member;

a deployment catheter operable to extend and deploy the anchor member therefrom, the deployment catheter including:

a handle;

a catheter body that is fixedly attached to the handle at one end, the anchor member and connected tensioning member being contained within a main lumen of the catheter body;

a spool assembly including a spool about which the tensioning member is routed, the spool having a first slip clutch portion; and a slip clutch assembly comprising the first slip clutch portion of the spool and a second slip clutch portion formed as part of a spool ratchet, the slip clutch assembly being configured to limit tension within the tensioning member as the tensioning member is pulled and wound about the spool as tension is applied to the anchor member, wherein the spool and spool ratchet rotate about a common axis;

wherein the spool ratchet is a separate part relative to the spool and includes a center hub that includes the second slip clutch portion and at least a portion of the center hub is received within a central bore formed in the spool, whereby the first and second slip clutch portions are operatively coupled to one another, wherein the spool ratchet includes an integral toothed wheel that operatively engages teeth of a spool lock member for controlling rotation of the spool ratchet, wherein the hub rotatably engages a retention member that is integrally formed along an inner surface of a housing of the handle for positioning and retaining the spool assembly inside the housing.

18. The system of claim 17, wherein the first slip clutch portion comprises a raised wall that includes a plurality of spaced recesses formed therein, the recesses being facing inward toward and open to the central bore of the spool and the second slip clutch portion comprises a plurality of flexible fingers, each finger having a detent formed at a free end thereof, the detents of the flexible fingers being received within respective recesses of the spool to couple the spool to the spool ratchet.

19. The system of claim 17, wherein the the spool lock is separate from the spool ratchet and is configured to restrict the spool ratchet from freely backspinning as the tensioning member is tensioned, wherein the spool lock is rotatably coupled to the housing.

20. The system of claim 17, wherein the spool and spool ratchet are coupled to one another and rotate in unison.

* * * * *